(12) United States Patent
Memering et al.

(10) Patent No.: US 9,863,927 B2
(45) Date of Patent: Jan. 9, 2018

(54) METHOD OF INSPECTING SAPPHIRE STRUCTURES AND METHOD OF FORMING THE SAME

(71) Applicant: Apple Inc., Cupertino, CA (US)

(72) Inventors: Dale N. Memering, San Francisco, CA (US); Matthew S. Rogers, San Jose, CA (US); Scott A. Myers, Palo Alto, CA (US)

(73) Assignee: APPLE INC., Cupertino, CA (US)

( * ) Notice: Subject to any disclaimer, the term of this patent is extended or adjusted under 35 U.S.C. 154(b) by 470 days.

(21) Appl. No.: 14/175,845

(22) Filed: Feb. 7, 2014

(65) Prior Publication Data

US 2015/0226723 A1    Aug. 13, 2015

(51) Int. Cl.
G01N 33/38 (2006.01)
G01N 21/958 (2006.01)
G01B 21/20 (2006.01)

(52) U.S. Cl.
CPC ......... *G01N 33/385* (2013.01); *G01N 21/958* (2013.01); *G01B 21/20* (2013.01)

(58) Field of Classification Search
CPC .... C03C 23/007; C03C 19/00; G01N 21/958; G01N 33/385
See application file for complete search history.

(56) References Cited

U.S. PATENT DOCUMENTS

2003/0186088 A1* 10/2003 Kato ................. C30B 23/02
428/698
2008/0180656 A1* 7/2008 Meeks ................ G01B 11/306
356/73

2013/0237402 A1* 9/2013 Wang ................ B24B 27/0633
501/86
2015/0089792 A1 4/2015 Memering et al.
2017/0089818 A1 3/2017 Bartlow et al.

FOREIGN PATENT DOCUMENTS

| CN | 1647228 | 7/2005 |
|---|---|---|
| CN | 203014915 | 6/2013 |
| JP | H02118615 | 5/1990 |
| JP | H04109709 | 4/1992 |
| JP | H10326385 | 12/1998 |

OTHER PUBLICATIONS

Gorla et al., "Structural, optical, and surface acoustic wave properties of epitaxial ZnO films grown on (0112) sapphire by metalorganic chemical vapor deposition," Journal of Applied Physics, vol. 85, No. 5, pp. 2594-2602, Mar. 1, 1999.
Wang et al., "Experimental study on ultrasonic crushing brazed diamond grits," Superhard Materials Engineering, vol. 23, No. 3, pp. 6-10, Jun. 30, 2011.

* cited by examiner

*Primary Examiner* — Thao X Le
*Assistant Examiner* — J. R. Oakley
(74) *Attorney, Agent, or Firm* — Brownstein Hyatt Farber Schreck, LLP

(57) ABSTRACT

A method of inspecting and forming sapphire structures. The method of inspecting a sapphire structure may include providing an annealed sapphire structure, and measuring a profile of at least a portion of the annealed sapphire structure. The profile of at least the portion of the annealed sapphire structure may be measured using a non-x-ray based measuring device. Additionally, the method of inspecting may include identifying a defect within at least a portion of the measured profile of the annealed sapphire structure.

14 Claims, 15 Drawing Sheets

METHOD OF INSPECTING SAPPHIRE STRUCTURES AND METHOD OF FORMING THE SAME

TECHNICAL FIELD

The disclosure relates generally to product inspection and manufacturing methods, and more particularly, to methods for inspecting and forming sapphire structures.

BACKGROUND

Current electronic devices continue to become more prevalent in day-to-day activities. For example, smart phones and tablet computers continue to grow in popularity, and provide everyday personal and business functions to its users. These electronic devices typically include large screens or displays utilized by the user to interact (e.g., input/output) with the electronic devices.

Conventionally these screens or displays are made from reinforced or modified glass. However, these glass screens may still be susceptible to damage. Specifically, these conventional screens may scratch, chip or crack when an undesirable impact event or force (e.g., drop, crushed) occurs with the electronic device. Damage to the screens of the electronic device may render the device partially, or completely, inoperable and/or may prevent the user from utilizing the electronic device for its intended purposes.

The use of the crystalline form of alumina ($Al_2O_3$) (e.g., Corundum), commonly known as sapphire, is becoming more of a viable option for replacing the glass screen or display. Specifically, with improved manufacturing processes of single crystal sapphire, and the improved elemental characteristics (e.g., hardness, strength) of sapphire over glass, sapphire may be an acceptable replacement material for conventional glass screens and displays. However, the same chemical/elemental characteristics that make sapphire a superior material choice over glass, also make the manufacturing of sapphire difficult. For example, sapphire utilized to make screens for electronic device typically undergo a final annealing process before further cosmetic process are performed. During this annealing process, the top surface of the sapphire may "heal," or fill in micro-cracks formed during other processes (e.g., lapping, cutting, planing). More specifically, surface atoms of the sapphire may be substantially mobile during the annealing process and may rearrange themselves to fill in the micro-cracks formed on the top surface.

However, in addition to filling these micro-cracks, the surface atoms may rearrange themselves during the annealing process to form a plurality of terraced protrusions in the top surface. These terraced protrusions may vary dependent upon a plurality of factors including, but not limited to, the crystallographic orientation of the sapphire and the operational characteristics (e.g., time, temperature, atmosphere) of the annealing process. While some terraced protrusions formed on the top surface of the sapphire may not negatively affect the quality of the sapphire, other protrusions may cause cosmetic defects in the sapphire. For example, some terraced protrusions may create colorful light reflections on the surface the sapphire. These reflections may negatively impact the sapphire when used as a screen or display for an electronic device by obstructing a user's ability to see the content featured on the screen of the electronic device clearly. That is, when a colorful light reflection occurs on the sapphire structure, that reflection may block or prevent a user from seeing at least a portion of the content being displayed on the screen. As a result, the functionality of the electronic device is diminished because of the cosmetic defect caused by the terraced protrusions formed on the sapphire's top surface.

SUMMARY

Generally, embodiments discussed herein are related to methods of inspecting sapphire structures and methods of forming the sapphire structure. The method of inspecting the sapphire structures may include measuring a profile of the sapphire structure, and determining if the top surface of the sapphire structure includes a defect. The defect of the top surface may be identified where the profile of the top surface includes a configuration that may not conform with an acceptable configuration. The measuring and subsequent identifying of this defect may be achieved using a non-x-ray based measuring device. As a result of being able to identify a defect in the top surface of the sapphire structure using a non-x-ray based measuring device, sapphire structures may be inspected more easily, more quickly and more cost-effectively, than conventional ways which include x-ray measuring devices. Additionally, each individual sapphire structure may be inspected using the method discussed herein. By inspecting the sapphire structures using the methods described herein, manufacturers may be able to improve quality control of the sapphire structure, and/or may examine every sapphire structure before it is implemented in its final function (e.g., screen for electronic device).

One embodiment may include a method of inspecting a sapphire structure. The method of inspecting may include providing an annealed sapphire structure, and measuring a profile of at least a portion of the annealed sapphire structure. The profile of at least the portion of the annealed sapphire structure may be measured using a non-x-ray based measuring device. Additionally, the method of inspecting may include identifying a defect within at least a portion of the measured profile of the annealed sapphire structure.

A further embodiment may include a method of forming a sapphire structure. The method may include treating at least a top surface of the sapphire structure, annealing the treated sapphire structure, and inspecting at least a portion of the top surface of the annealed sapphire structure. The portion of the top surface of the annealed sapphire structure may be inspected using a non-x-ray based measuring device. The method of forming the sapphire structure may also include identifying a defect within the inspected portion of the top surface of the annealed sapphire structure. Additionally, in response to identifying a defect within the inspected portion of the top surface of the annealed sapphire structure, the method may include at least one of: re-treating the inspected portion of the annealed sapphire structure, and re-annealing the inspected portion of the annealed sapphire structure.

BRIEF DESCRIPTION OF THE DRAWINGS

The disclosure will be readily understood by the following detailed description in conjunction with the accompanying drawings, wherein like reference numerals designate like structural elements, and in which.

Figure 1:
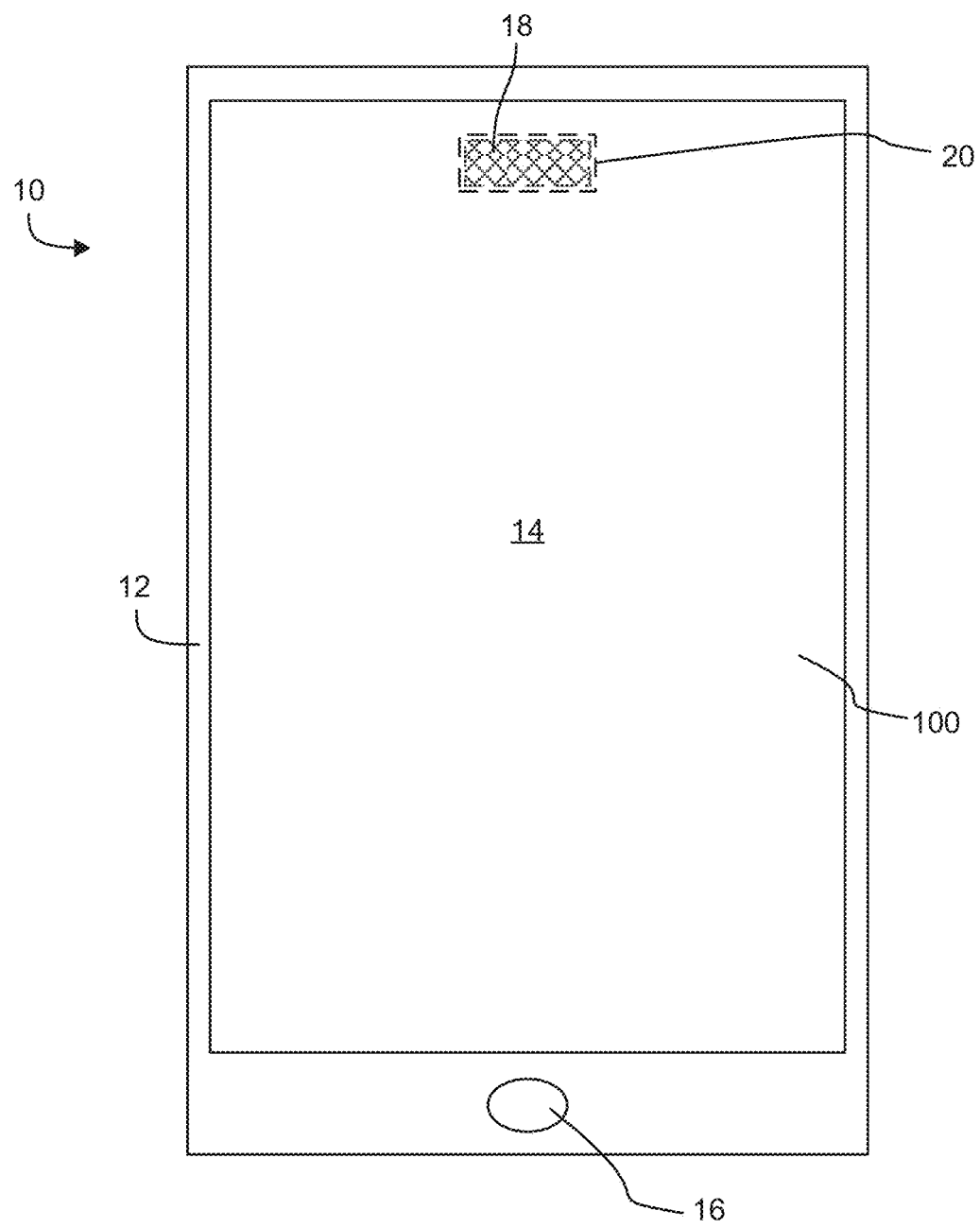
FIG. 1 shows an illustrative plane view of an electronic device including a sapphire structure, according to embodiments.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims The following disclosure relates generally to product inspection and manufacturing methods, and more particularly, to methods for inspecting and forming sapphire structures.

In a particular embodiment, a method of inspecting a sapphire structures may include measuring a profile of the sapphire structure, and determining if the top surface of the sapphire structure includes a defect. The defect of the top surface may be identified where the profile of the top surface includes a configuration that may not conform with an acceptable configuration. The measuring and subsequent identifying of this defect may be achieved using a non-x-ray based measuring device. As a result of being able to identify a defect in the top surface of the sapphire structure using a non-x-ray based measuring device, sapphire structures may be inspected more easily, more quickly and more cost-effectively, than conventional ways which include x-ray measuring devices. Additionally, each individual sapphire structure may be inspected using the method discussed herein. By inspecting the sapphire structures using the methods described herein, manufacturers may be able to improve quality control of the sapphire structure, and/or may examine every sapphire structure before it is implemented in its final function (e.g., screen for electronic device).

The method of inspecting a sapphire structure may include providing an annealed sapphire structure, and measuring a profile of at least a portion of the annealed sapphire structure. The profile of at least the portion of the annealed sapphire structure may be measured using a non-x-ray based measuring device. Additionally, the method of inspecting may include identifying a defect within at least a portion of the measured profile of the annealed sapphire structure.

The method of forming may include treating at least a top surface of the sapphire structure, annealing the treated sapphire structure, and inspecting at least a portion of the top surface of the annealed sapphire structure. The portion of the top surface of the annealed sapphire structure may be inspected using a non-x-ray based measuring device. The method of forming the sapphire structure may also include identifying a defect within the inspected portion of the top surface of the annealed sapphire structure. Additionally, in response to identifying a defect within the inspected portion of the top surface of the annealed sapphire structure, the method may include at least one of: re-treating the inspected portion of the annealed sapphire structure, and re-annealing the inspected portion of the annealed sapphire structure.

These and other embodiments are discussed below with reference to FIGS. 1-6H. However, those skilled in the art will readily appreciate that the detailed description given herein with respect to these Figures is for explanatory purposes only and should not be construed as limiting.

Referring now to FIG. 1, there is shown a plane perspective view of one example of an electronic device 10 that can include, or be connected to a biometric sensing device (not shown). In the illustrated embodiment, electronic device 10 is implemented as a smart telephone. Other embodiments can implement the electronic device 10 differently, such as, for example, as a laptop or desktop computer, a tablet computing device, a gaming device, a display, a digital music player, a wearable computing device or display such as a watch or glasses, and other types of electronic devices that can receive biometric data from a biometric sensing device.

The electronic device 10 includes a casing 12 at least partially surrounding a display 14 and one or more button assemblies 16. Enclosure 12 can form an outer surface or partial outer surface and protective case for the internal components of electronic device 10, and may at least partially surround display 14. Enclosure 12 can be formed of one or more components operably connected together, such as a front piece and a back piece. Alternatively, enclosure 12 can be formed of a single piece operably connected to the display 14. Button assembly 16 may be utilized by electronic device 10 to provide user input and/or allow the user to interact with the various functions of electronic device 10.

Additionally, where electronic device 10 is implemented as a smart telephone, electronic device 10 may also include a speaker component 18 positioned within enclosure 12. As shown in FIG. 1, display 14 may include an opening 20 formed through the display 14, where opening 20 may be in alignment with speaker component 18 of electronic device 10. Opening 20 may be formed through display 14 to substantially prevent obstruction of the sound emitted by speaker component 18 during operation of electronic device 10.

Display 14 can be implemented with any suitable technology, including, but not limited to, a multi-touch sensing touchscreen that uses liquid crystal display (LCD) technology, light emitting diode (LED) technology, organic light-emitting display (OLED) technology, organic electroluminescence (OEL) technology, or another type of display technology. Electronic device 10 may include a sapphire structure 100 covering display 14. More specifically, sapphire structure 100 may be included in electronic device 10 as a protective layer or window included in display 14. Sapphire structure 100 may be the external component or surface of display 14, and may allow a user to interact with the electronic device 10, without contacting and/or harming the internal components (e.g., liquid crystal, circuitry, and the like) of display 14 and device 10.

Figure 2:
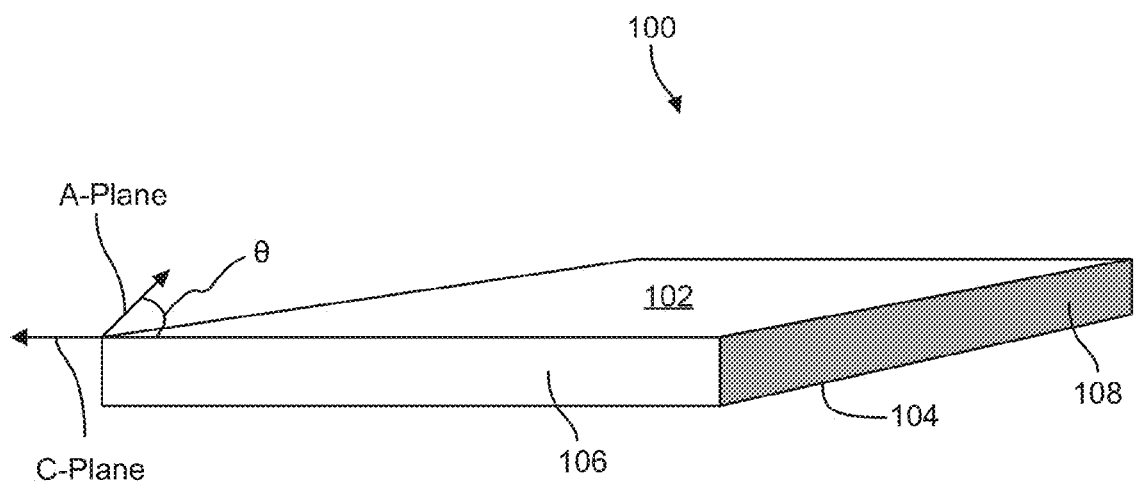
FIG. 2 shows an illustrative perspective view of a sapphire structure, according to embodiments.

Turning to FIG. 2, a perspective view of a sapphire structure 100 is shown according to embodiments of the invention. Sapphire structure 100, as shown in FIG. 2, may be a pre-cut piece of artificially grown corundum to be used in electronic device 10 of FIG. 1. The artificially grown corundum used to form sapphire structure 100 may be grown using any conventional growth process including, but not limited to: hydrothermal growth; vertical horizontal gradient freezing ("VHGF"); edge-defined film-fed growth ("EFG"); horizontal moving growth (e.g., Bridgman growth); and Kyropoulos growth.

Sapphire structure 100 may include a top surface 102 and a bottom surface 104 positioned opposite top surface 102. When included or implemented in electronic device 10 (FIG. 1), top surface 102 may be exposed to a user for interacting with electronic device 10, and bottom surface 104 may be positioned substantially within enclosure 12 of electronic device 10. Sapphire structure 100 may be retained within enclosure 12 of electronic device 10 using any conventional coupling technique including, but not limited to: snap-fit, compression fit, adhesive, weld, and bonding. For example, sapphire structure 100 may be coupled to enclosure 12 by including an adhesive on bottom surface 104 and/or sidewalls 106, 108. That is, sapphire structure 100 may be inserted into enclosure 12, and the adhesive on bottom surface 104 and/or sidewalls 106, 108 may contact a portion of enclosure 12, to couple sapphire component 100 within enclosure 12 to protect and/or provide a window to display 14. As shown in FIG. 2, sidewalls 106, 108 may be substantially perpendicular to top surface 102 and bottom surface 104, respectively. However, it is understood that sidewalls 106, 108 may be substantially angled relative to top surface 102 for fitting and retaining sapphire structure 100 within enclosure 12 of electronic device 10. For example, where sidewalls 106, 108 include substantially angled surfaces, a portion of enclosure 12 adjacent display 14 may include a conversely angled surface to abut and/or contact the angled sidewall 106, 108 to fix sapphire structure 100 within enclosure 12. Additional configurations for sidewalls 106, 108 of sapphire structure 100 for retaining sapphire structure 100 within enclosure may also be understood. For example, sidewalls 106, 108 may include a protrusion portion (not shown) for contacting a portion of enclosure 12 to substantially fix sapphire structure 100 within enclosure 12.

As shown in FIG. 2, sapphire structure 100 may also include a plurality of plane orientations for the surfaces (e.g., top surface 102, sidewalls 106, 108) of sapphire structure 100. More specifically, each of the surfaces of sapphire structure 100 may be in alignment with a crystallographic plane orientation determined by the formation of sapphire structure 100. For example, as shown in FIG. 2, top surface 102 may include an offset A-plane crystallographic orientation, while sidewall 106 may include a C-plane crystallographic orientation. Top surface 102 may be offset from the A-plane crystallographic orientation by a determinable degree ($\theta$). The offset determinable degree ($\theta$) may be a result of an error in the initial processes of forming sapphire structure 100. For example, and as discussed herein, sapphire structure 100 may not be cut from a large piece of grown corundum at a desired crystallographic plane (C-plane), but rather may be cut at an offset degree ($\theta$) from the desired plane.

It is understood that corundum (e.g., sapphire) is an anisotropic material. As a result, the crystallographic orientation of the surfaces of components made from corundum or sapphire (e.g., sapphire structure 100) may affect the physical properties and/or material characteristics (e.g., strength, ductility, elasticity) of the component. It is also understood that the crystallographic orientation of the various surfaces (e.g., top surface 102, sidewalls 106, 108) may be dependent on the growing processes used for creating the corundum of sapphire structure 100 and/or the cutting process for forming sapphire structure 100 from the corundum. For example, the corundum from which sapphire structure 100 is formed may be grown using an EFG growth process. In the growth process, the seed crystal may include a plane orientation to yield corundum that may allow for specific, desired planes (e.g., C-plane, A-plane) to be utilized in components formed from the corundum (e.g., sapphire structure 100). By knowing the orientation of the seed crystal used in the EFG growth process, and ultimately knowing the crystallographic orientation of the grown corundum, manufactures can cut the corundum in a specific direction to form components with surfaces having specific plane crystallographic orientations, or substantially desirable plane crystallographic orientations.

Figure 3:
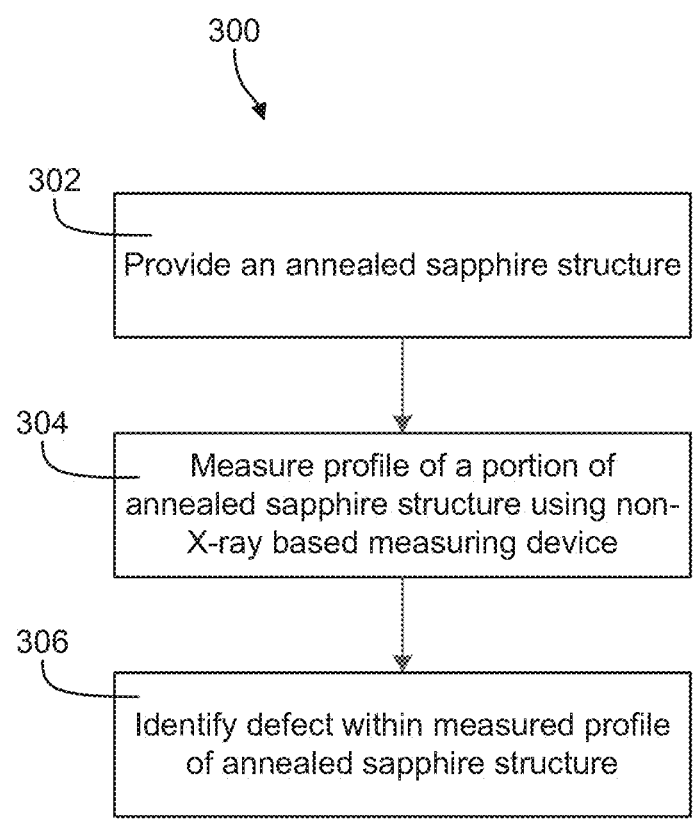
FIG. 3 is a flow chart illustrating a method for inspecting a sapphire structure. This method may be performed on a sapphire structure as shown in FIGS. 1 and 2.

Turning to FIG. 3, a method for inspecting a sapphire structure (see, FIGS. 4A-4G) is now discussed. Specifically, FIG. 3 is a flowchart depicting one sample method 300 for inspecting an annealed sapphire structure.

In operation 302, the annealed sapphire structure may be provided. The annealing process performed on the annealed sapphire structure, as discussed herein, may include the application of heat at an annealing temperature to the sapphire structure, over a predetermined annealing time, at a predetermined atmospheric pressure. Additionally, and as discussed herein, the annealing process performed on the sapphire structure may be performed to substantially "heal" and/or correct imperfections (e.g., cracks, gaps) on a top surface of the sapphire structure. The imperfections may be formed in the top surface while performing the initial processes (e.g., grinding, lapping, planning, cutting, polishing) for creating the annealed sapphire structure.

The annealing of the sapphire structure may also create additional features on the top surface of the sapphire structure. More specifically, the performing of an annealing process on the sapphire structure may result in the formation of a plurality of terrace protrusions formed on the top surface of the sapphire structure. The plurality of terraced protrusions are formed as a result of the corundum, used to form the annealed sapphire structure, typically including surface atoms having substantial mobility during an annealing process. That is, during the annealing process, these surface atoms of the sapphire structure may be able to move about the top surface of the sapphire structure. Due to the surface atom's mobility, the annealing process may be performed on the sapphire structure to allow the surface atoms to move and subsequently heal/fill-in any cracks or gaps that may be formed in the top surface during previous processing of the sapphire structure. However, because of the mobility of the surface atoms, and the anisotropic properties of the annealed sapphire structure, the atoms may also substantially move and/or arrange themselves in configuration that requires the least amount of energy. Typically, this causes the surface atoms to rearrange themselves to be in substantial alignment with a crystallographic plane of the annealed sapphire structure. As briefly discussed above, and discussed in detail below, where a plane of the annealed sapphire structure is offset by an angle (e.g., FIG. 2, $\theta$), the surface atoms will rearrange themselves into a terraced protrusion formation on the top surface of the sapphire structure.

Figure 4A:
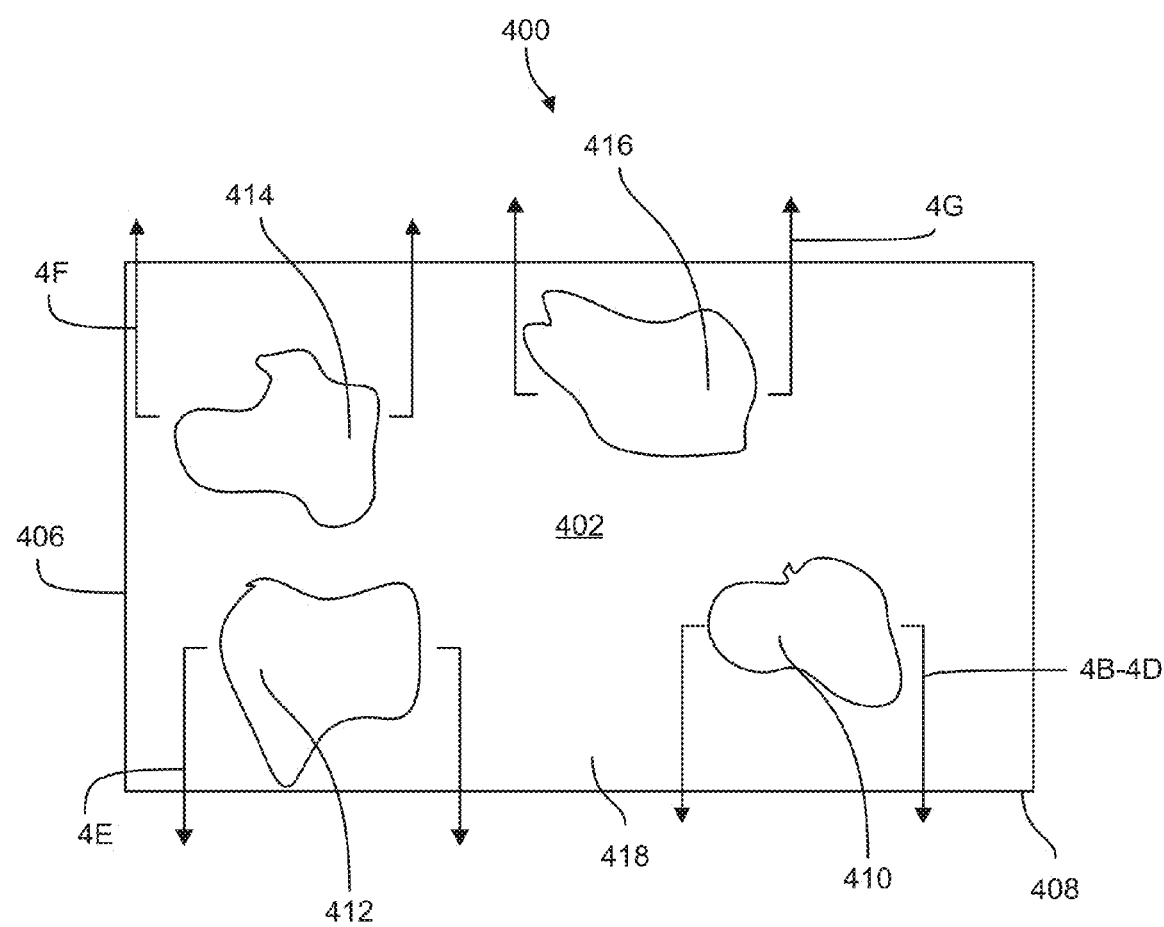
FIG. 4A shows an illustrative plane view of an annealed sapphire structure undergoing processes of inspecting as depicted in FIG. 3, according to embodiments.
Figure 4B:
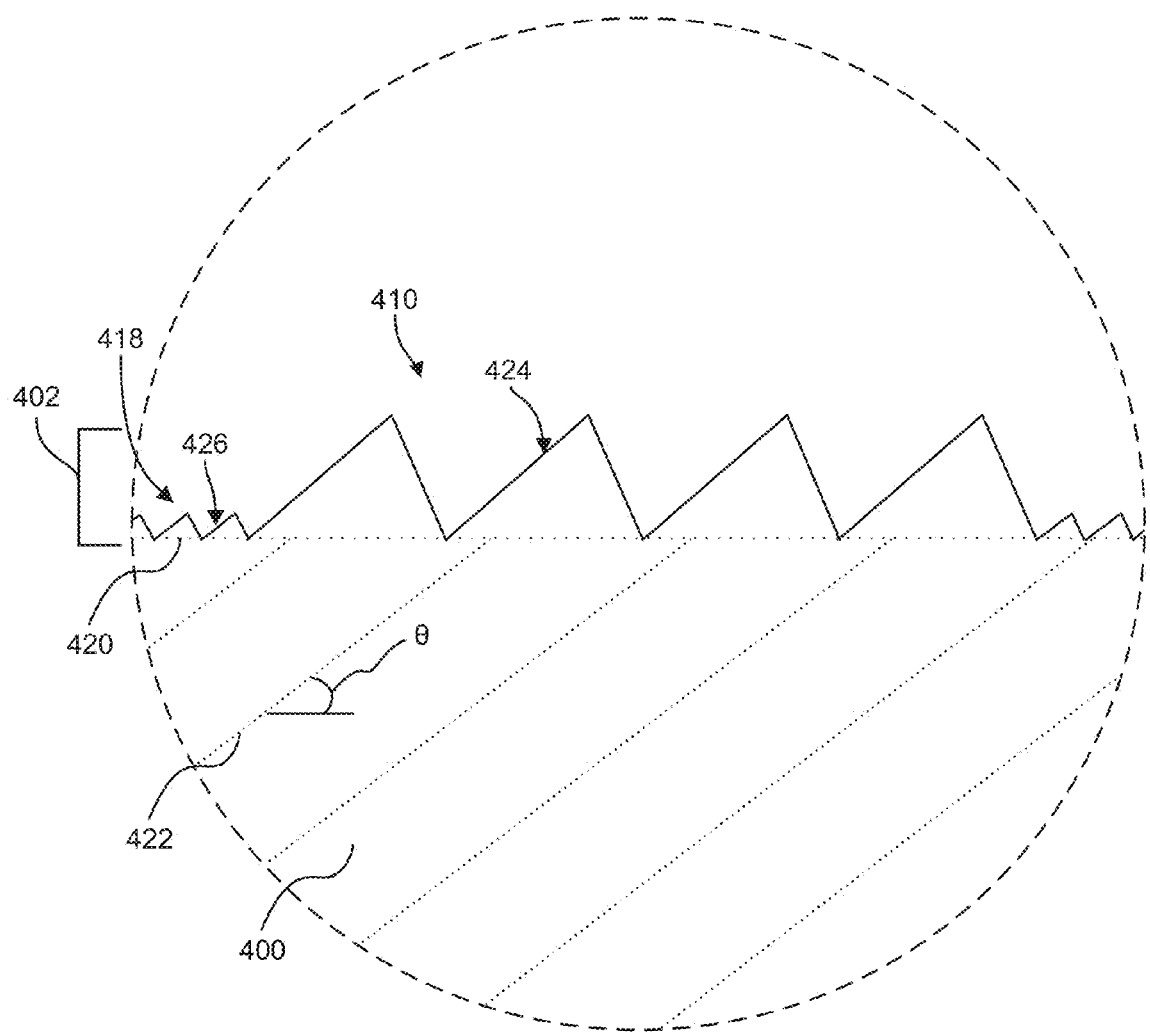
FIGS. 4B-4G show illustrative front cross-sectional views of a portion of the annealed sapphire structure of FIG. 4A undergoing processes of inspection as depicted in FIG. 3, according to embodiments.
Figure 4C:
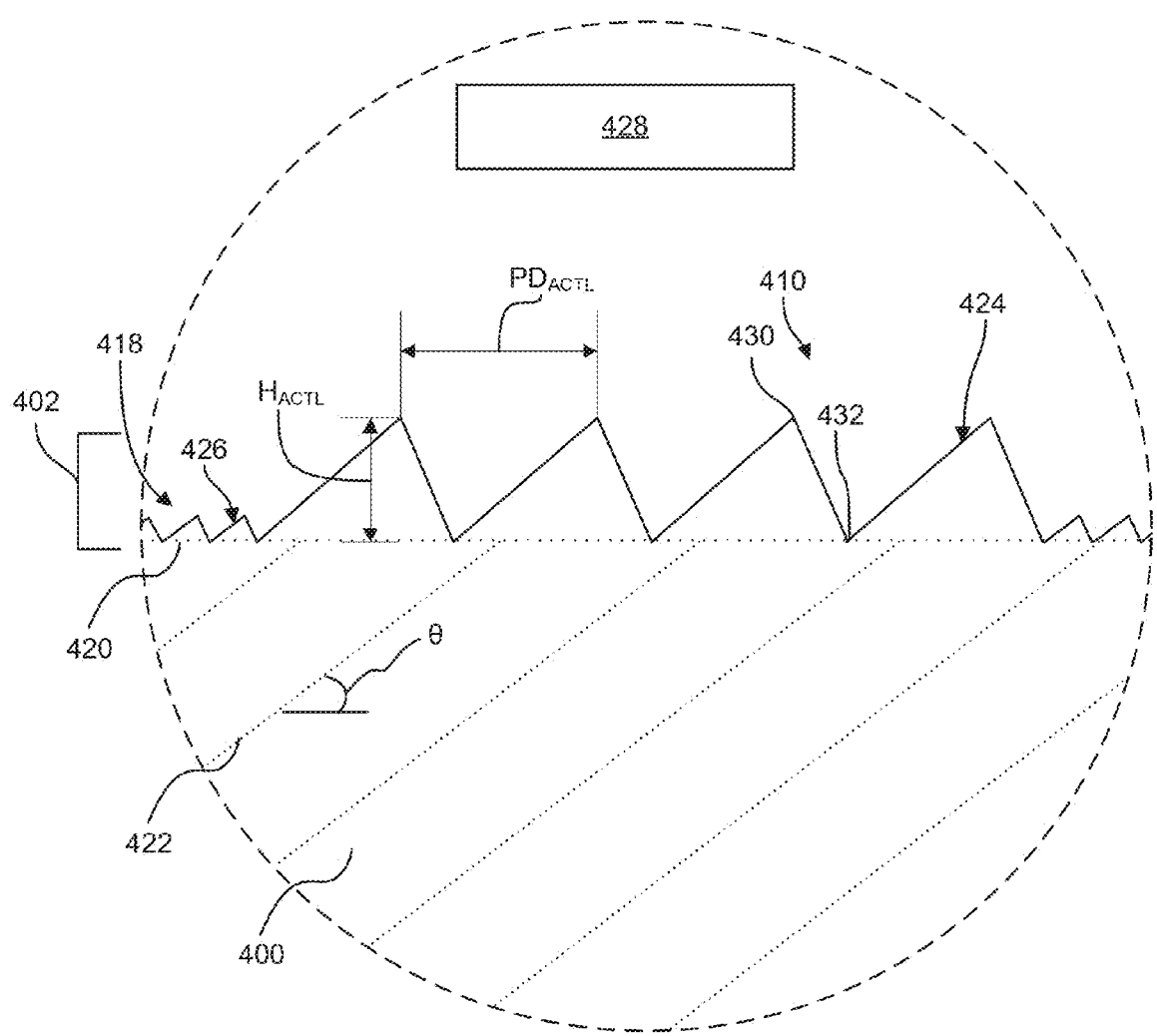

In operation 304, a profile of a portion of the annealed sapphire structure may be measured using a non-x-ray based measuring device (see, FIG. 4C, non-x-ray device 428). The measuring of the profile may include determining the geometry of the plurality of terraced protrusions included in the annealed sapphire structure. More specifically, the measuring of the profile may include determining an actual height and actual peak-to-peak or peak distance of each of the plurality of terraced protrusions formed in the top surface of the annealed sapphire structure.

The non-x-ray based measuring device, utilized in operation 304, may include a variety of conventional measuring devices configured to measure a profile of a portion of the annealed sapphire structure. More specifically, the non-x-ray based measuring device may include a differential interference contrast (DIC) microscope, an interferometer, a profilometer, or any other conventional non-x-ray based measuring device that may be capable of depicting a profile of the sapphire structure. The non-x-ray based measuring device may be utilized by a user (e.g., quality control inspector, manufacturer, etc.) or by an automated system configured to perform the inspection process as discussed herein with respect to FIG. 3.

In operation 306, a defect may be identified within the portion of the measured profile of the annealed sapphire structure. The identifying of the defect of the annealed sapphire structure may include comparing the actual height and peak distance of the plurality of terraced protrusions, determined in operation 304, with respective predetermined acceptable heights and predetermined acceptable peak distances. As discussed herein, the predetermined acceptable height and the predetermined acceptable peak distance may include a maximum height and peak distance, respectively, for the sapphire structure that may be substantially free from the defect. Where the actual height and/or peak distance exceed the predetermined acceptable height and/or peak distance, a defect may be identified, as discussed herein. The defect of the annealed sapphire structure may include a substantially undesirable, optical defect formed in the top surface. More specifically, where the defect includes an optical defect caused by terraced protrusions formed on the top surface during the annealing process, the annealed sapphire structure may include undesirable, colorful light reflections on the top surface when the sapphire structure is exposed to light. When the sapphire structure including the optical defect is implemented within electronic device 10 (see, FIG. 1), the optical defects may substantially obstruct a user's ability to see display 14, which may undesirably reduce the intended functionality of electronic device 10.

Turning to FIGS. 4A-4G, a plane and side cross-sectional views of various portions of an annealed sapphire structure 400 undergoing method 300, as depicted in FIG. 3, are shown. It is understood that similarly numbered components may function in a substantially similar fashion. Redundant explanation of these components has been omitted for clarity.

As shown in FIG. 4A, annealed sapphire structure 400 may be provided. The providing of annealed sapphire structure 400 in FIG. 4A may correspond to operation 302 in FIG. 3. Annealed sapphire structure 400 may be substantially similar to sapphire structure 100 discussed herein with respect to FIG. 2. However, annealed sapphire structure 400, as shown in FIG. 4A, may have undergone an annealing process. The annealing process performed on annealed sapphire structure 400, as discussed herein, may include the application of heat at an annealing temperature to annealed sapphire structure 400, over a predetermined annealing time, at a predetermined atmospheric pressure. Additionally, and as discussed herein, the annealing process performed on annealed sapphire structure 400 may be performed to substantially "heal" and/or correct imperfections (e.g., cracks, gaps) on top surface 402.

As shown in FIG. 4A, top surface 402 may include a plurality of distinct terraced protrusion portions 410, 412, 414, 416. More specifically, top surface 402 of annealed sapphire structure 400 may include a plurality of distinct portions including terraced protrusions 410, 412, 414, 416 formed during the annealing process. As discussed herein, the plurality of terraced protrusions 410, 412, 414, 416, are formed on top surface 402 as a result of the corundum used to form annealed sapphire structure 400 typically including surface atoms having substantial mobility during an annealing process of annealed sapphire structure 400. That is, during the annealing process, these surface atoms of annealed sapphire structure 400 may be able to move about top surface 402 of sapphire structure. Due to the surface atom's mobility, the annealing process may be performed on annealed sapphire structure 400 to allow the surface atoms to move and subsequently heal/fill-in any cracks or gaps that may be formed in top surface 402 during previous processing of annealed sapphire structure 400. However, because of the mobility of the surface atoms, and the anisotropic properties of annealed sapphire structure 400, the atoms may also substantially move and/or arrange themselves in configuration that requires the least amount of energy. Typically, this causes the surface atoms to rearrange themselves to be in substantial alignment with a crystallographic plane of annealed sapphire structure 400. As briefly discussed above, and discussed in detail below, where a plane of annealed sapphire structure 400 is offset by an angle (e.g., FIG. 2, θ), the surface atoms will rearrange themselves into a terraced protrusion formation 410, 412, 414, 416.

Each of the plurality of distinct terraced protrusion 410, 412, 414, 416 may be distinct from each other, and from other portions of top surface 402 of annealed sapphire structure 400. More specifically, as shown in FIG. 4A, and discussed herein, each of the distinct plurality of terraced protrusion portions 410, 412, 414, 416 of top surface 402 may be configured with distinct dimensions from each other and from the remaining portion 418 (e.g., unpatterned) of top surface 402. The remaining portion 418 (e.g., unpatterned) of top surface 402 may also include terraced protrusions as a result of the rearrangement of the surface atoms of annealed sapphire structure 400 during the annealing process. However, the terraced protrusions positioned in remaining portion 418 of top surface 402 may be substantially negligible and/or may not cause a defect within annealed sapphire structure 400, as discussed herein. The discrepancies in the configurations of the distinct terraced protrusion portions 410, 412, 414, 416, and remaining portion 418 (e.g., unpatterned) may be cause by a plurality of factors including, but not limited to: the predetermined annealing temperature of the annealing process, the predetermined annealing time of the annealing process, the predetermined atmospheric pressure of the annealing process, the method of applying the heat, imperfections on top surface 402 of annealed sapphire structure 400, and the crystallographic orientation of the surfaces (e.g., top surface 402, sidewall 406, 408) of annealed sapphire structure 400.

Turning to FIG. 4B, a cross-sectional front view of terrace protrusions 410 of annealed sapphire structure 400 is shown according to embodiments. More specifically, a profile of terraced protrusions 410 and a portion of remaining portion 418 of top surface 402 is shown in FIG. 4B. As discussed herein, the profile and/or configuration of top surface 402 including terraced protrusions 410, as shown in FIG. 4B, may be formed as a result of the moving of the surface atoms of annealed sapphire structure 400 during the annealing process. For reference, the substantially horizontal phantom line of FIG. 4B-4G may represent pre-annealing top surface 420 of annealed sapphire structure 400.

Also shown in FIG. 4B, annealed sapphire structure 400 may include a plane 422 having a crystallographic orientation. More specifically, plane 422 of annealed sapphire structure 400 may be substantially offset by an angle (θ) when compared to pre-annealing top surface 420 (shown in phantom). As discussed above, during the annealing process surface atoms may rearrange themselves in a configuration that requires the least amount of energy. As a result, each of the plurality of terraced protrusions 410 of top surface 402 may be in substantial alignment with plane 422 of annealed sapphire structure 400. More specifically, and as shown in FIG. 4B, a protrusion face 424 of each of the plurality of terraced protrusions 410 and a protrusion face 426 of the protrusions of remaining portion 418 may be in parallel alignment with plane 422. The plane crystallographic orientation 422 may include any conventional plane of corundum (e.g., A-plane, C-plane, M-plane).

As discussed herein, the terraced protrusions formed in remaining portion 418 may include a substantially small height and peak-to-peak distance (hereafter, "peak distance"). By comparison, terraced protrusions 410 formed in top surface 402 may be substantially larger in both height and peak distance when compared to the terraced protrusions of remaining portion 418. The configuration and/or dimensions of terraced protrusions 410 of top surface 402 may indicate that a defect is present within top surface 402 of annealed sapphire structure 400. That is, and as discussed herein, because of the configuration of the terraced protrusions 410, the portion of top surface 402 of annealed sapphire structure 400 including terraced protrusions 410 may require further inspection processes to determine if terraced protrusions 410 may cause a defect within annealed sapphire structure 400.

As shown in FIG. 4C, non-x-ray measuring device 428 (hereafter, "non-x-ray device") may measure the profile of terraced protrusions 410 formed in a portion of top surface 402 of annealed sapphire structure 400. Utilizing non-x-ray device 428 to measure the profile of terraced protrusions 410 of annealed sapphire structure 400 may correspond to operation 304 of FIG. 3. As discussed herein, the measuring of the profile by non-x-ray device 428 may include determining an actual height ($H_{ACTL}$) and actual peak-to-peak or peak distance ($PD_{ACTL}$) of the plurality of terraced protrusions 410 of the measured portion of top surface 402 of annealed sapphire structure 400. As shown in FIG. 4C, each of the plurality of terraced protrusions 410 formed in top surface 402 may include a peak 430, which may be the highest point formed in terraced protrusions 410 during the annealing process. During the annealing process, the surface atoms that may form peak 430 may move the furthest from pre-annealing top surface 420 (shown in phantom) to allow face 424 of terraced protrusions 410 to be in substantial alignment with plane 422. Additionally, each of the plurality of terraced protrusions 410 may also include a base point 432, which may be in substantial alignment with pre-annealing top surface 420 (shown in phantom). Distinct from the atoms forming peak 430, the surface atoms of that form base point 432 may move minimally, or not all, during the annealing process, and may remain in a substantially similar position as prior to the annealing of annealed sapphire structure 400. The actual height ($H_{ACTL}$) of terraced protrusion 410 may be the distance between base point 432 and/or pre-annealing top surface 420 and peak 430. Additionally, the actual peak distance ($PD_{ACTL}$) of terraced protrusions 410 of annealed sapphire structure 400 may be the distance between two distinct peaks 430. As discussed herein, the actual height ($H_{ACTL}$) and/or the actual peak distance ($PD_{ACTL}$) of the terraced protrusion 410 formed in top surface 402 of sapphire structure 400 may be directly correlated to the presence of a defect within top surface 402 of annealed sapphire structure 400.

As shown in FIG. 4B the actual height ($H_{ACTL}$) and the actual peak distance ($PD_{ACTL}$) for each of the protrusions of terraced protrusions 410 may be substantially similar and uniform. As such, the measured actual height ($H_{ACTL}$) of a single protrusion of terrace protrusions 410, and the measured actual peak distance ($PD_{ACTL}$) between two protrusions of terrace protrusions 410 is shown in FIG. 4B. However, it is understood that each of the plurality of terraced protrusions (e.g., terraced protrusions 410) formed on top surface 402 during an annealing process may be distinct from one another, which may require the measuring of most or substantially all terraced protrusion formed in top surface 402. More specifically, each of the plurality of terraced protrusions may include a distinct actual height ($H_{ACTL}$) and/or actual peak distance ($PD_{ACTL}$). As such, the majority, if not all, of the plurality of terraced protrusions may be measured for completeness of inspecting annealed sapphire structure 400.

Prior to measuring, non-x-ray device 428 may also be utilized to determine the protrusions of remaining portion 418 may not cause a potential defect within annealed sapphire structure 400. More specifically, an intermediate process may be performed prior to the measuring of the profile of sapphire structure 400. The intermediate process may include examining the substantially small protrusions of remaining portion 418, and determining the protrusions of remaining portion 418 are negligible with respect to inspecting sapphire structure 400. That is, because the terraced protrusions formed on remaining portion 418 are substantially small, there may be substantially no chance that the protrusions found in remaining portion 418 may include a defect. As discussed herein, because of the small configuration and/or dimensions of the protrusions of remaining portion 418, and the subsequent determination that the protrusions of remaining portion 418 are negligible within respect to the inspection process, no additional inspection process may be performed on the protrusions of remaining portion 418. As a result, the inspection of sapphire structure 400 may include a substantially reduced time and/or cost to the manufacturer of sapphire structure 400.

Figure 4D:
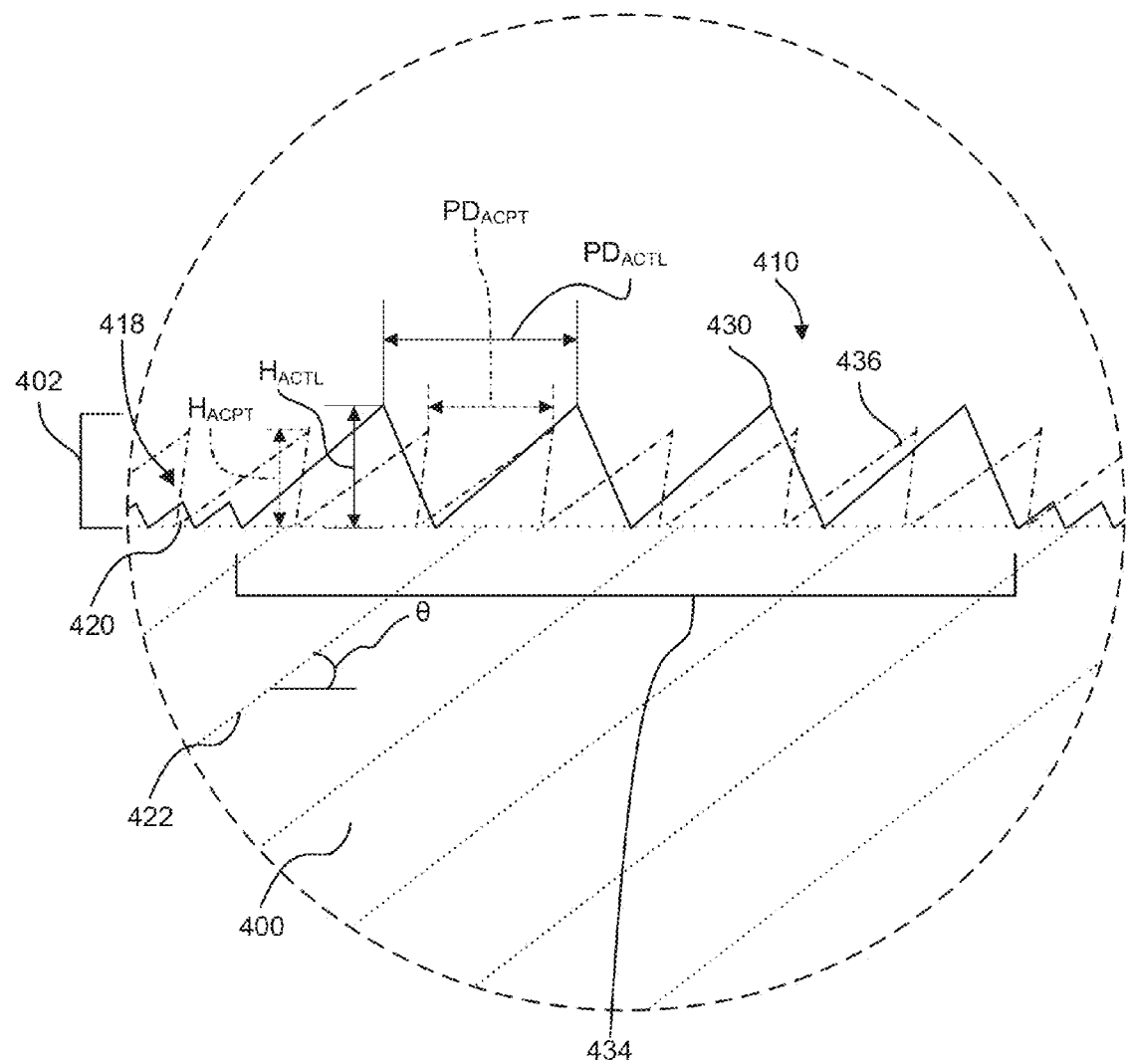

As shown in FIG. 4D, defect 434 may be identified as terraced protrusions 410 formed in a portion of top surface 402 of annealed sapphire structure 400. More specifically, the plurality of protrusions of top surface 402 forming terraced protrusions 410 may be identified as defect 434 of sapphire structure 400. The identifying of defect 434 in FIG. 4D may correspond to operation 306 of FIG. 3. As discussed herein, defect 434 of annealed sapphire structure 400 may include a substantially undesirable, optical defect formed in top surface 402. More specifically, where defect 434 includes an optical defect caused by terraced protrusions (e.g., terraced protrusions 410) formed on top surface 402, annealed sapphire structure 400 may include undesirable, colorful light reflections on surface 402 when sapphire structure 400 is exposed to light.

As shown in FIG. 4D, and discussed herein, the identifying of defect 434 of annealed sapphire structure 400 may include comparing the actual height ($H_{ACTL}$) and peak distance ($PD_{ACTL}$) of the plurality of terraced protrusions 410 of top surface 402 with respective predetermined acceptable heights ($H_{ACPT}$) and predetermined acceptable peak distances ($PD_{ACPT}$). That is, the identifying of defect 434 may include comparing the actual height ($H_{ACTL}$) of the plurality of terraced protrusions 410 of top surface 402 with a predetermined acceptable height ($H_{ACPT}$) for sapphire structure 400. Additionally, the identifying of defect 434 may include comparing the actual peak distance ($PD_{ACTL}$) of the plurality of terraced protrusions 410 of top surface 402 with a predetermined acceptable peak distance ($PD_{ACPT}$) for sapphire structure 400. The predetermined acceptable height ($H_{ACPT}$) and the predetermined acceptable peak distance ($PD_{ACPT}$) may include a height and peak distance, respectively, of acceptable terraced protrusions 436 (shown in phantom) for annealed sapphire structure 400. The acceptable terraced protrusions 436 for annealed sapphire structure 400 may include the upper-limit dimensions for terraced protrusions formed during the annealing process, where acceptable terraced protrusions 436 of top surface 402, and ultimately annealed sapphire structure 400, are substantially free from defect 434. That is, acceptable terraced protrusions 436 may include dimensions that represent the maximum height (H) and peak distance (PD) for terraced protrusions formed on top surface 402 of annealed sapphire structure 400, where annealed sapphire structure 400 may be free and/or may not include defect 434.

The identifying of defect 434, and more specifically, the comparing of the actual height ($H_{ACTL}$) and peak distance ($PD_{ACTL}$) with the predetermined acceptable heights ($H_{ACPT}$) and predetermined acceptable peak distances ($PD_{ACPT}$), respectively, may further include determining if the actual height ($H_{ACTL}$) and peak distance ($PD_{ACTL}$) differ from the predetermined acceptable heights ($H_{ACPT}$) and acceptable peak distances ($PD_{ACPT}$). That is, defect 434 may be identified in annealed sapphire structure 400 by comparing and determining if the actual height ($H_{ACTL}$) of terraced protrusions 410 differ from the predetermined acceptable heights ($H_{ACPT}$) of acceptable terraced protrusions 436. Additionally, defect 434 may be identified in annealed sapphire structure 400 by comparing and determining if the actual peak distance ($PD_{ACTL}$) of terraced protrusions 410 differ from the predetermined acceptable peak distance ($PD_{ACPT}$) of acceptable terraced protrusions 436. As shown in FIG. 4D, both the actual height ($H_{ACTL}$) and peak distance ($PD_{ACTL}$) of the terraced protrusions 410 formed on top surface 402 may be larger than or exceed the predetermined acceptable heights ($H_{ACPT}$) and acceptable peak distances ($PD_{ACPT}$), respectively. More specifically, when comparing the actual height ($H_{ACTL}$) of the terraced protrusions 410 with the predetermined acceptable heights ($H_{ACPT}$) of acceptable terraced protrusions 436 of annealed sapphire structure 400, it may be determined that the actual height ($H_{ACTL}$) is larger than the predetermined acceptable heights ($H_{ACPT}$). Additionally, by comparing the actual peak distance ($PD_{ACTL}$) of the terraced protrusions 410 with the predetermined acceptable peak distance ($PD_{ACPT}$) of acceptable terraced protrusions 436, it may also be determined that the actual peak distance ($PD_{ACTL}$) is greater than the predetermined acceptable peak distance ($PD_{ACPT}$). As such, terraced protrusions 410 of top surface 402 may be identified as defect 434 within annealed sapphire structure 400. As discussed herein, a portion or the entirety of annealed sapphire structure 400 may be further processed when defect 434 is identified, to remove or substantially correct defect 434 of annealed sapphire structure 400.

In additional embodiments, terraced protrusions 412, 414, 416 formed in top surface 402 of annealed sapphire structure 400 may include distinct configurations or dimensions, which ultimately may or may not result in defect 434 of annealed sapphire structure 400.

Figure 4E:
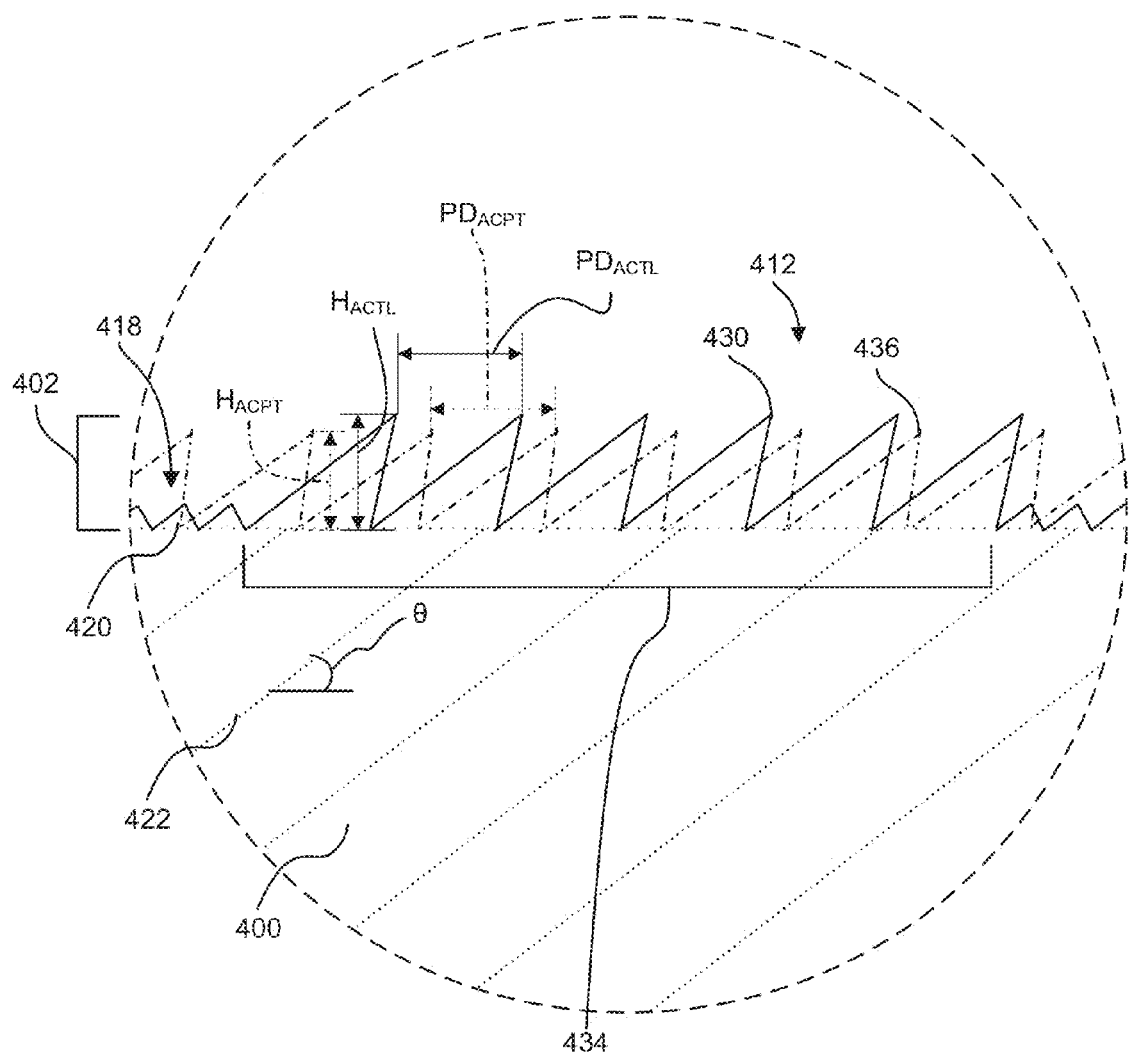

For example, FIG. 4E depicts a cross-sectional front profile view of the plurality of terraced protrusions 412 formed in top surface 402 of annealed sapphire structure 400. It is understood that similarly numbered components may function in a substantially similar fashion. Redundant explanation of these components has been omitted for clarity. As shown in FIG. 4E, Defect 434 may also be identified in terraced protrusions 412 formed in top surface 402. However, the identifying of defect 434 in terraced protrusions 412 may be distinct from the identifying of defect 434 within terraced protrusions 410 (FIGS. 4A and 4D). More specifically, the configuration or dimensions of terraced protrusions 412 may be distinct from terraced protrusions 410 (FIGS. 4A and 4D), which may ultimately cause the identifying of defect 434 of annealed sapphire structure 400 to be distinct as well. The identifying of defect 434 in terraced protrusion 412 may be performed in a substantially similar manner as discussed with respect to FIG. 4D. However, because of terraced protrusions 412 distinct configuration or dimensions when compared to terraced protrusions 410, the outcome of the identifying process may be distinct. For example, and with comparison to the identifying of defect 434 within terraced protrusions 410 (FIG. 4D), the actual height ($H_{ACTL}$) of peaks 430 for terraced protrusions 412 may be compared to the predetermined acceptable heights ($H_{ACPT}$) of acceptable terraced protrusions 436 of annealed sapphire structure 400. In comparing the respective heights (e.g., $H_{ACTL}$, $H_{ACPT}$), it may be determined that the actual height ($H_{ACTL}$) of terraced protrusions 412 differs from the predetermined acceptable heights ($H_{ACPT}$) of acceptable terraced protrusions 436. More specifically, it may be determined that the actual height ($H_{ACK}$) of terraced protrusions 412 is larger than the predetermined acceptable heights ($H_{ACPT}$) of acceptable terraced protrusions 436. However, in comparing the actual peak distance ($PD_{ACTL}$) of terraced protrusions 412 and the predetermined acceptable peak distance ($PD_{ACPT}$) of acceptable terraced protrusions 436, it may be determined that the respective peak distances (e.g., $PD_{ACTL}$, $PD_{ACPT}$) are substantially equal to one another. That is, the actual peak distance ($PD_{ACTL}$) of terraced protrusions 412 and the predetermined acceptable peak distance ($PD_{ACPT}$) of acceptable terraced protrusion 436 may be substantially equal. Where the actual peak distance ($PD_{ACTL}$) and the predetermined acceptable peak distance ($PD_{ACPT}$) are substantially equal, the actual peak distance ($PD_{ACTL}$) of terraced protrusion 412 may not be attributed to the cause of defect 434 in annealed sapphire structure 400. As a result, in the embodiment shown in FIG. 4E, only the actual height ($H_{ACTL}$), and not the actual peak distance ($PD_{ACTL}$), of terraced protrusion 412 may be attributed to causing defect 434 within annealed sapphire structure 400. As discussed herein, where defect 434 is attributed only to the actual height ($H_{ACTL}$) of terraced protrusions (e.g., terraced protrusions 412) formed in top surface 402 of annealed sapphire structure 400, specific additional processes may be performed on annealed sapphire structure 400 to substantially correct defect 434.

Figure 4F:
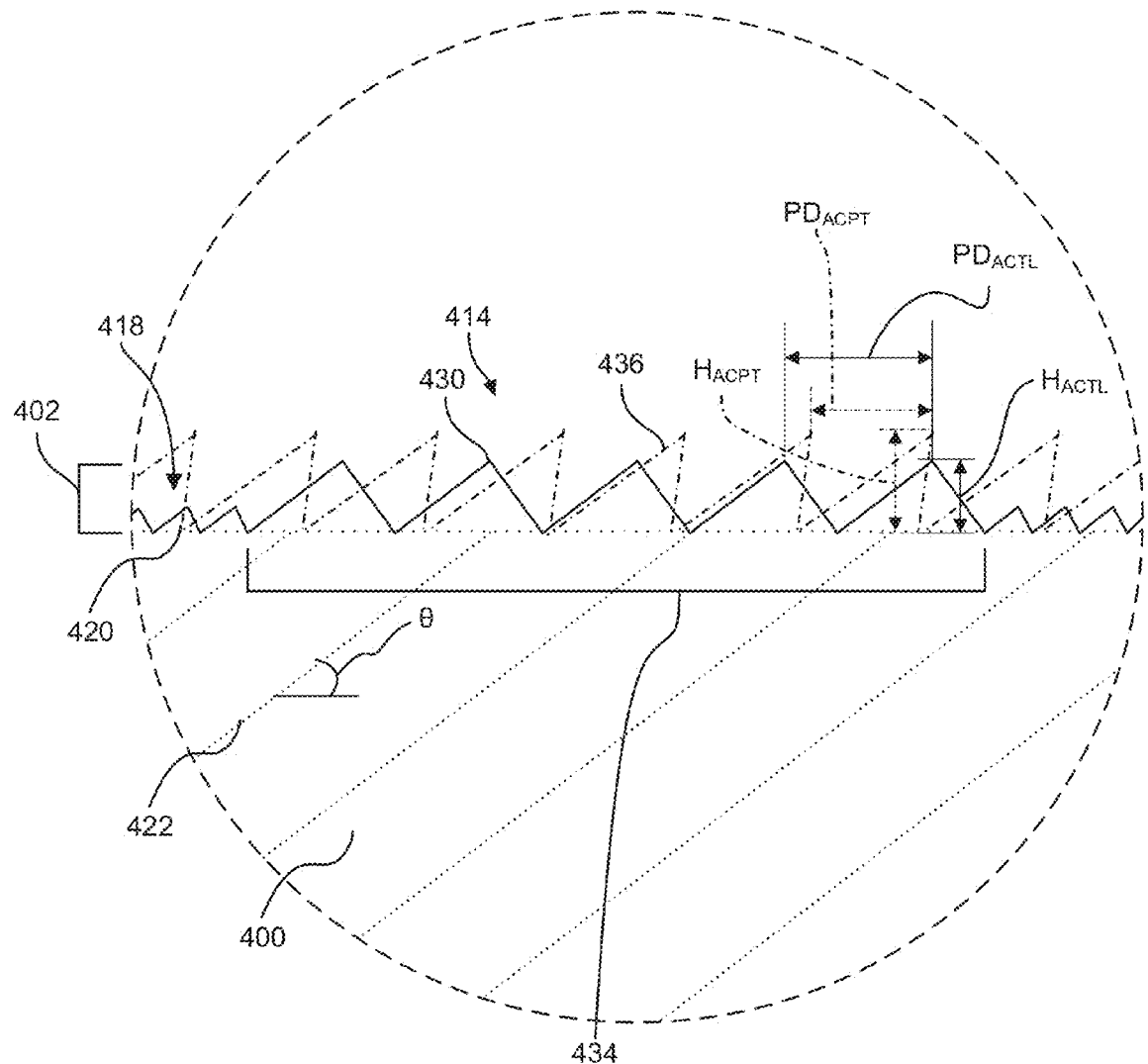

In an additional embodiment, as shown in FIG. 4F, the converse to the embodiment discussed with respect to FIG. 4E may be shown. More specifically, FIG. 4F shows a cross-sectional front profile view of the plurality of terraced protrusions 414 formed in top surface 402 of annealed sapphire structure 400. Terraced protrusions 414 of annealed sapphire surface 400 may include defect 434 identified using similar processes as discussed above. However, and with comparison to terraced protrusions 412 shown in FIG. 4E, defect 434 may be identified as a result of a distinct outcome of the identifying process. In comparing the respective heights (e.g., $H_{ACTL}$, $H_{ACPT}$), it may be determined that the actual height ($H_{ACTL}$) of terraced protrusions 414 differs from the predetermined acceptable heights ($H_{ACPT}$) of acceptable terraced protrusions 436. More specifically, it may be determined that the actual height ($H_{ACTL}$) of terraced protrusions 414 is smaller than the predetermined acceptable heights ($H_{ACPT}$) of acceptable terraced protrusions 436. Because, the actual height ($H_{ACTL}$) of terraced protrusions 414 is smaller than the predetermined acceptable heights ($H_{ACPT}$) (e.g., maximum acceptable height), the actual height ($H_{ACTL}$) of terraced protrusions 414 may not be attributed to the cause of defect 434 in annealed sapphire structure 400. However, in comparing the actual peak distance ($PD_{ACTL}$) of terraced protrusions 414 and the predetermined acceptable peak distance ($PD_{ACPT}$) of acceptable terraced protrusions 436, it may be determined that the respective peak distances (e.g., $PD_{ACTL}$, $PD_{ACPT}$) substantially differ. That is, the actual peak distance ($PD_{ACTL}$) of terraced protrusions 412 is larger the predetermined acceptable peak distance ($PD_{ACPT}$) of acceptable terraced protrusion 436. As a result, in the embodiment shown in FIG. 4F, only the actual peak distance ($PD_{ACTL}$), and not the actual height ($H_{ACTL}$), of terraced protrusion 414 may be attributed to causing defect 434 within annealed sapphire structure 400. As discussed herein, where defect 434 is attributed only to the actual peak distance ($PD_{ACTL}$) of terraced protrusions (e.g., terraced protrusions 414) formed in top surface 402 of annealed sapphire structure 400, specific additional processes may be performed on annealed sapphire structure 400 to substantially correct defect 434.

Figure 4G:
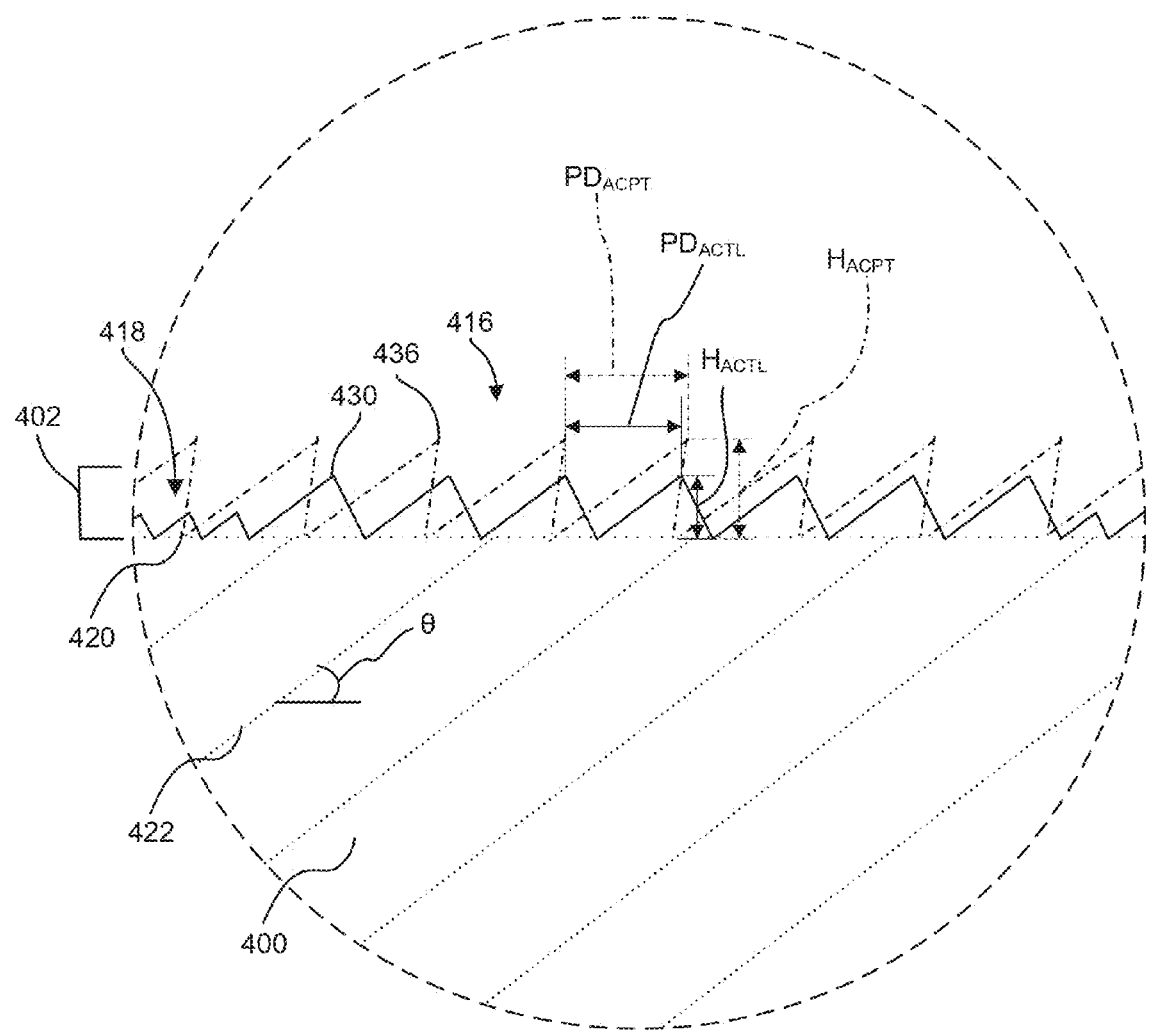

In a further embodiment, as shown in FIG. 4G, terraced protrusions 416 formed on top surface 402 of annealed sapphire structure 400 may not include defect 434 (FIGS. 4D-4F). FIG. 4G shows a cross-sectional front profile view of the plurality of terraced protrusions 416 formed in top surface 402 of annealed sapphire structure 400. Terraced protrusions 416 of annealed sapphire surface 400 may not include defect 434 like the distinct terraced protrusions 410, 412, 414 of annealed sapphire structure 400. The identifying processes discussed herein may be used to determine that terraced protrusions 416 may not include defect 434. More specifically, the actual height ($H_{ACTL}$) and peak distance ($PD_{ACTL}$) of terraced protrusions 416 may be compared with the predetermined acceptable heights ($H_{ACPT}$) and predetermined acceptable peak distances ($PD_{ACPT}$), respectively, of acceptable terraced protrusion 436 of annealed sapphire structure 400. As shown in FIG. 4G, it may also be determined that the actual height ($H_{ACTL}$) and peak distance ($PD_{ACTL}$) of terraced protrusions 416 differ from the predetermined acceptable heights ($H_{ACPT}$) and acceptable peak distances ($PD_{ACPT}$). That is, the actual height ($H_{ACTL}$) of terraced protrusions 416 may be smaller than, or within the maximum acceptable dimensions, as defined by the predetermined acceptable heights ($H_{ACPT}$) of acceptable terraced protrusions 436 of annealed sapphire structure 400. Similarly, the actual peak distance ($PD_{ACTL}$) of terraced protrusions 416 may also be smaller than, or within the maximum acceptable dimensions, as defined by the predetermined acceptable peak distance ($PD_{ACPT}$) of acceptable terraced protrusions 436. As a result, the identifying process discussed herein may determine that terraced protrusions 416 of annealed sapphire structure 400 do not include defect 434 (FIG. 4D-4F). As such, terraced protrusions 416 may not require further processing, and may be acceptable for annealed sapphire structure 400 to be utilized within electronic device 10 (FIG. 1).

As discussed herein, as a result of being able to identify defect 434 in the top surface 402 of the sapphire structure 400 using a non-x-ray based measuring device 428, sapphire structures 400 may be inspected more easily, more quickly and more cost-effectively, than conventional ways which include x-ray measuring devices. Additionally, each individual sapphire structure 400 may be inspected using the method discussed herein. By inspecting the sapphire structures 400 using the methods described herein, manufacturers may be able to improve quality control of the sapphire structure 400, and/or may examine every sapphire structure 400 before it is implemented in its final function (e.g., screen for electronic device 10).

The use of non-x-ray device 428 may also help indicate that sapphire structures 400 are being formed within a desired plane, or include an acceptable offset (e.g., θ) of a desired plane. That is, by identifying an orientation of face 424 of terraced protrusions 410, 412, 414, 416 non-x-ray device 428 may also aid in performing a quality control check as well. As discussed above, face 424 may formed in substantial alignment with plane 422 of sapphire structure 400. Additionally, each sapphire structure 400 may be made with a desired plane or offset (e.g., θ) of a desired plane in order to be acceptable for use within electronic device 10 (FIG. 1). Typically, these planes are measure on a large piece of grown corundum using an x-ray diffraction methods, and not the plurality of sapphire structures 400 formed from the grown corundum. This minimal check of orientation may be a result of the cost and time associated with x-ray diffraction. However, by utilizing non-x-ray device 428, each sapphire structure 400 formed form the grown corundum may be inspected. Specifically, by determining the desired crystallographic plane orientation of the corundum using initial x-ray diffraction methods, non-x-ray device 428 may examine and compare the desired crystallographic plane orientation of the corundum and the orientation of face 424 of terraced protrusions 410 to determine if annealed sapphire structure 400 includes an crystallographic orientation in alignment with the desired crystallographic orientation. That is, as discussed herein, face 424 of terraced protrusions 410 may align itself with the crystallographic orientation of sapphire structure 400. Therefore, the orientation of face 424 is substantially similar to the orientation of annealed sapphire structure 400. As such, where orientation of face 424 is compared to, and differs drastically from the desired crystallographic plane orientation of the corundum, it may be determined that sapphire structure 400 is being formed within an undesirable crystallographic plane orientation. As such, processes of forming sapphire structure 400 (e.g., grinding, lapping, cutting) may require adjustments, so face 424 of terraced protrusions 410, 412, 414, 416 of annealed sapphire structure 400 are substantially equal to the desired plane.

Figure 5:
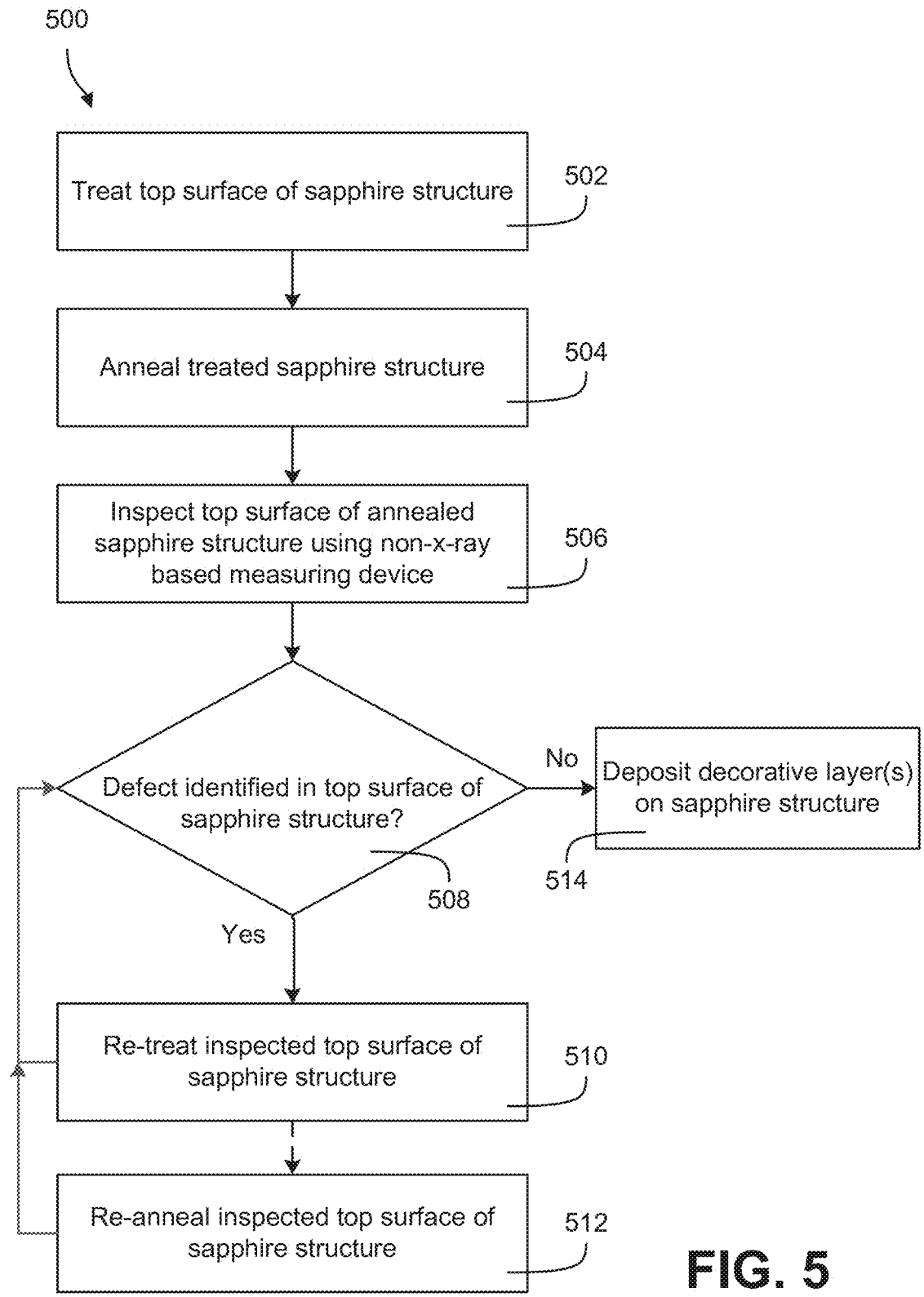
FIG. 5 is a flow chart illustrating a method of forming a sapphire structure, according to embodiments.
Figure 6A:
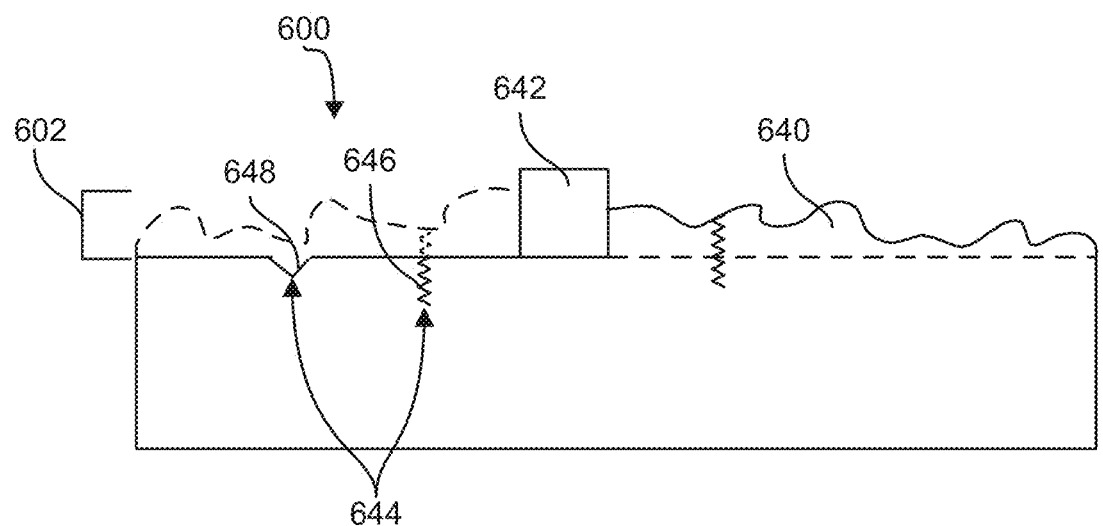
FIGS. 6A-6H show illustrative front cross-sectional views of a portion of a sapphire structure undergoing processes of formation as depicted in FIG. 5, according to embodiments.
Figure 6B:
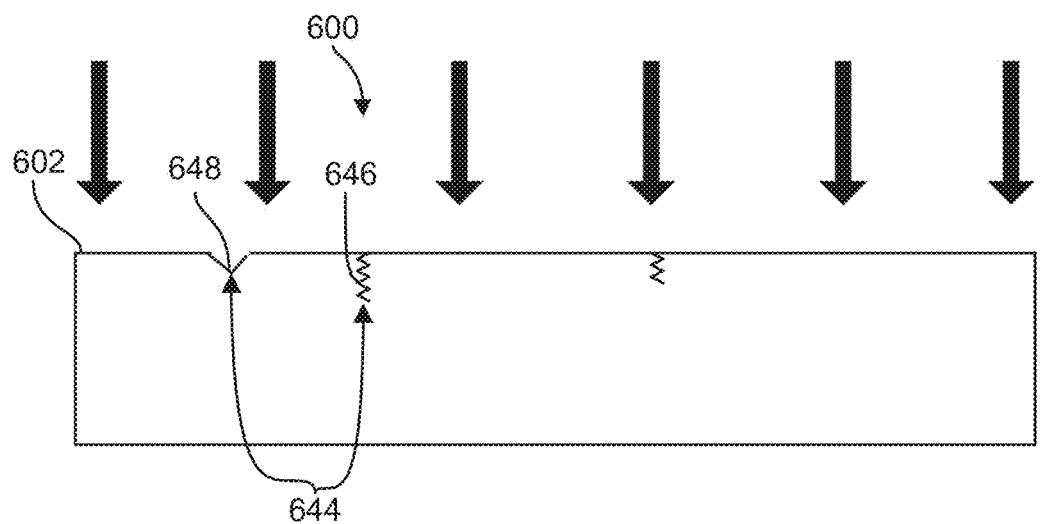
Figure 6C:
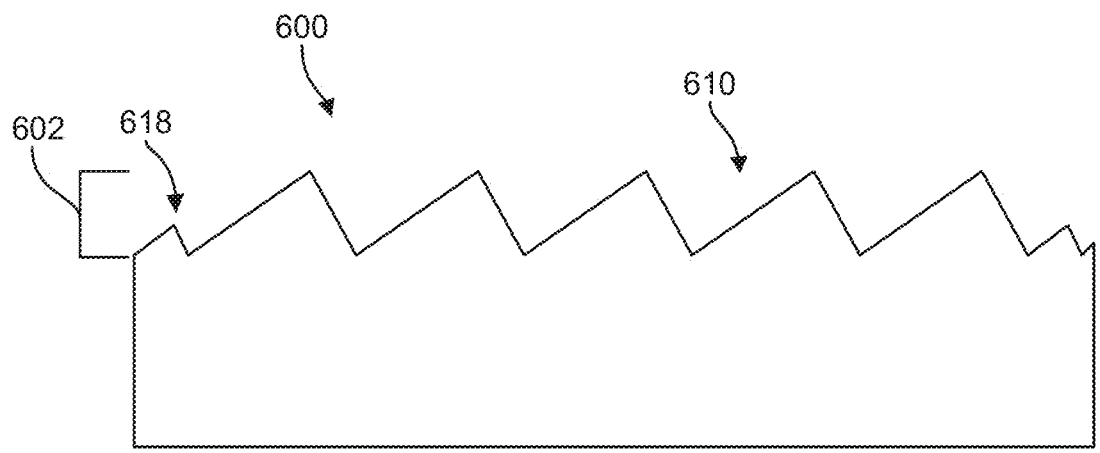
Figure 6D:
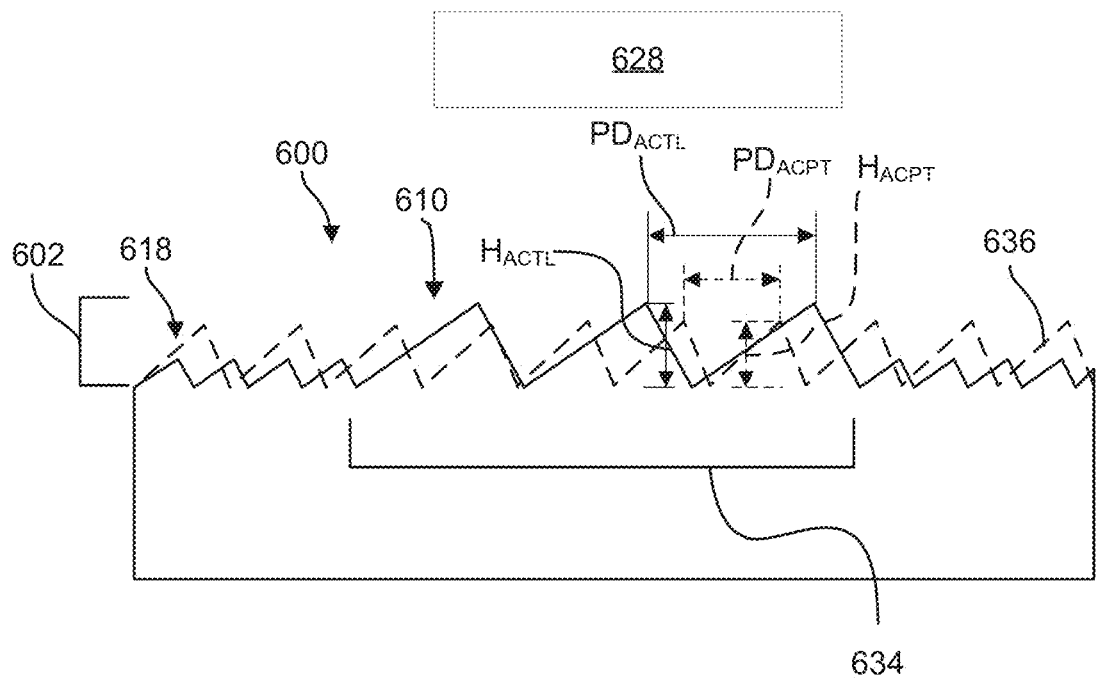
Figure 6E:
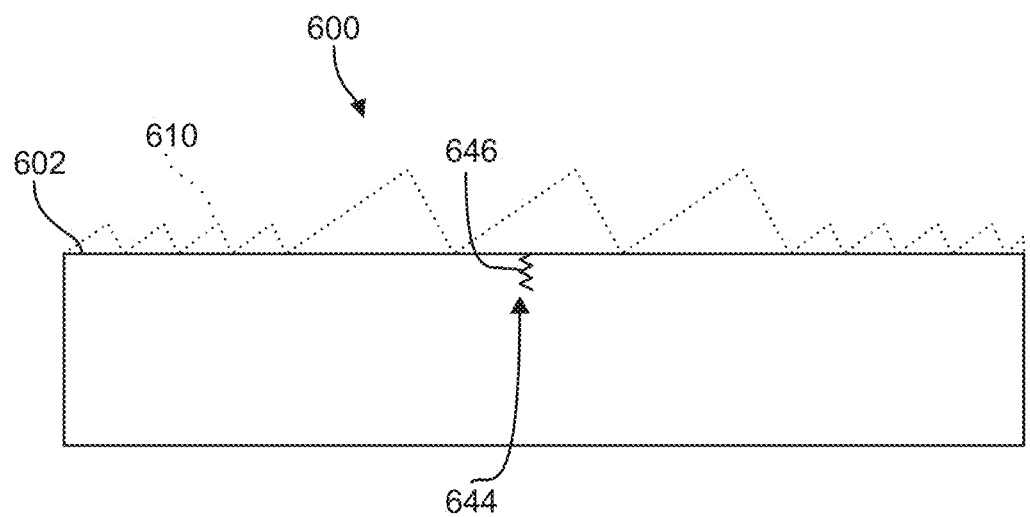
Figure 6F:
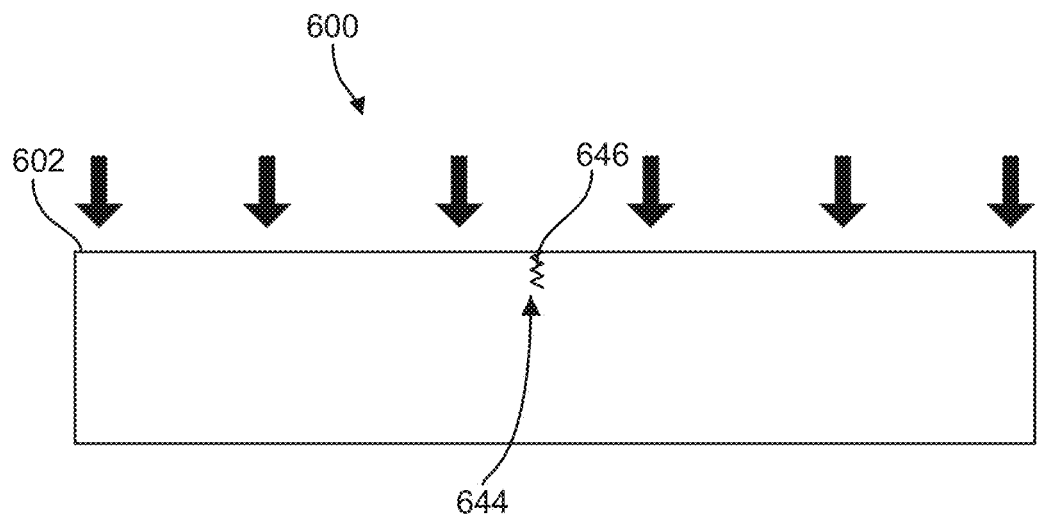
Figure 6G:
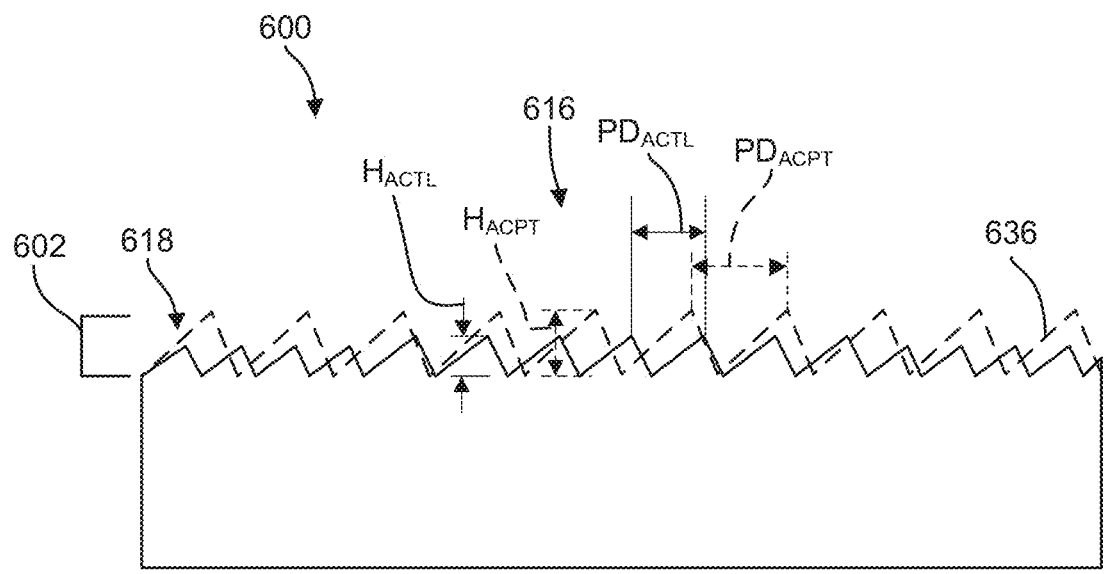
Figure 6H:
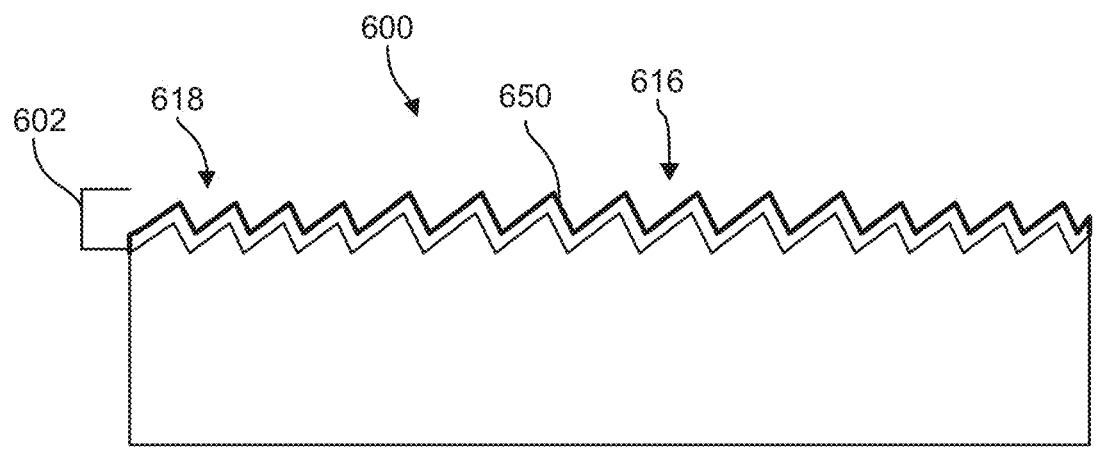

Turning to FIGS. 5-6H, a method for forming sapphire structure 600 may now be discussed. Specifically, FIG. 5 is a flowchart depicting one sample method 500 for forming sapphire structure 600. FIGS. 6A-6H may depict a side cross-sectional view of various portions of sapphire structure 600 undergoing method 500, as depicted in FIG. 5. It is understood that similarly numbered components may function in a substantially similar fashion. Redundant explanation of these components has been omitted for clarity.

In operation 502, at least top surface 602 of sapphire structure 600 may be treated. As shown in FIG. 6A, a cross-sectional front view of a portion of sapphire structure 600 is shown. The process of treating sapphire structure 600 may be depicted in FIG. 6A. The process of treating at least top surface 602 of sapphire structure 600 in operation 502 may include lapping sapphire structure 600 and polishing lapped top surface 602 of sapphire structure 600. As shown in FIG. 6A, a polishing process being performed on sapphire structure 600 is depicted. Sapphire structure 600 may be previously lapped, such that sapphire structure 600 may include a substantially desired thickness. As shown in FIG. 6A, top surface 602 of sapphire structure 600 may be substantially non-uniform and may include a plurality of ridges 640. The plurality of ridges 640 may be formed during the lapping process of sapphire structure 600. The polishing process performed on sapphire structure 600 may substantially remove the plurality of ridges 640. More specifically, as shown in FIG. 6A, polishing device 642 may perform a polishing process on sapphire structure 600 for substantially removing the plurality of ridges 640 formed during a lapping process and configuring top surface 602 to include a substantially linear surface. The treating process of operation 502 may include any conventional lapping and/or polishing techniques typically used in the formation of sapphire structure 600. More specifically, the lapping techniques may include, but are not limited to grinding-lapping, or soft-material lapping, and the polishing techniques may include, but are not limited to chemical mechanical polishing, flame polishing, or vapor polishing.

As shown in FIG. 6A, the treating of top surface 602 of sapphire structure 600 in operation 502 may cause a plurality of imperfections 644 in top surface 602. More specifically, during the lapping and/or the polishing process performed on top surface 602 of sapphire structure 600 may cause imperfections 644, such as cracks 646 and/or gaps 648, to be formed in sapphire structure 600. The cracks 646 and/or gaps 648 may be formed in top surface 602 and may extend partially through sapphire structure 600. As discussed herein, annealing sapphire structure 600 may aid in healing and/or fixing these imperfections 644 (e.g., cracks 646, gaps 648) in sapphire structure 600.

In operation 504, treated sapphire structure 600 may be annealed. As shown in FIG. 6B, sapphire structure 600 may undergo an annealing process. More specifically, sapphire structure 600 may be exposed to a predetermined annealing temperature, for a predetermined annealing time, in a predetermined annealing atmospheric pressure to substantially anneal sapphire structure 600. The annealing process of operation 504 may be performed on sapphire structure 600 to heal and/or correct imperfections 644 (e.g., cracks 646, gap 648). That is, with comparison to FIGS. 6B and 6C, annealing process of operation 504 may substantially heal and/or correct imperfections 644 formed on sapphire structure 600 during the treating process in operation 502. FIG. 6C may depict sapphire structure 600 after the annealing process of operation 504 is complete. As discussed in detail above, during the annealing process, the surface atoms of sapphire structure 600 may be substantially mobile, such that the surface atoms rearrange themselves to heal or correct imperfections 644 of sapphire structure 600. Additionally as discussed in detail above, and shown in FIG. 6C, the surface atoms of sapphire structure 600 may substantially rearrange themselves to formed terraced protrusions 610 in top surface 602 of sapphire structure 600. That is, the annealing of sapphire structure 600 may include forming the plurality of distinct terrace protrusions 610 on top surface 602 of sapphire structure 600, as discussed herein.

In operation 506, at least a portion of top surface 602 of sapphire structure 600 may be inspected using non-x-ray based measuring device 628. As shown in FIG. 6D, and as similarly discussed with reference to FIGS. 3-4G above, non-x-ray device 628 may be utilized to inspect a profile of sapphire structure 600. The inspection of top surface 602 of sapphire structure 600 in operation 506 may include similar processes as discussed above. More specifically, the inspection of top surface 602 in operation 506 may include measuring a profile of top surface 602 of sapphire structure 600 after the annealing process. The measuring of the profile of top surface 602 may include determining an actual height ($H_{ACTL}$) of terraced protrusions 610, and determining an actual peak distance ($PD_{ACTL}$) between peaks 630 of terraced protrusions 610, as discussed above.

In operation 508, defect 634 may be identified in the inspected portion of top surface 602 of sapphire structure 600. Returning to FIG. 6D, defect 634 may be identified using substantially similar processes as discussed above. That is, the identifying of defect 634 in sapphire structure 600 may include comparing the actual height ($H_{ACTL}$) and peak distance ($PD_{ACTL}$) of terraced protrusions 610 with the predetermined acceptable height ($H_{ACPT}$) and predetermined acceptable peak distance ($PD_{ACPT}$) of acceptable terraced protrusions 636 (shown in phantom) of sapphire structure 600. Additionally, in comparing the respective heights (e.g., $H_{ACTL}$, $H_{ACPT}$) and peak distances ($PD_{ACTL}$, $PD_{ACPT}$), the identifying may also include determining if the actual height ($H_{ACTL}$) and peak distance ($PD_{ACTL}$) differ from the predetermined acceptable height ($H_{ACPT}$) and peak distance ($H_{ACPT}$), respectively. As discussed herein, where the actual height ($H_{ACTL}$) and peak distance ($PD_{ACTL}$) differ from, and more specifically exceed the predetermined acceptable height ($H_{ACPT}$) and peak distance ($P_{DACPT}$), defect 634 may be included in terraced protrusions 610 of sapphire structure 600.

As shown in FIG. 6D, both the actual height ($H_{ACTL}$) and peak distance ($PD_{ACTL}$) of terraced protrusions 610 exceed the respective predetermined acceptable height ($H_{ACPT}$) and peak distance ($P_{DACPT}$) of acceptable terraced protrusion 636 of sapphire structure 600. As such, further processing (e.g., operations 510 and/or 512) may be performed on sapphire structure 600. As discussed herein, where the actual height ($H_{ACTL}$) and peak distance ($PD_{ACTL}$) of terraced protrusions 610 do not differ or exceed the respective predetermined acceptable height ($H_{ACPT}$) and peak distance ($P_{DACPT}$) of acceptable terraced protrusion 636 of sapphire structure 600, final, cosmetic processes (e.g., operation 514) may be performed on sapphire structure 600.

In operation 510, top surface 602 of sapphire structure 600 may be re-treated in response to identifying defect 634 in sapphire structure 600 in operation 508. As shown in FIG. 6E, after identifying defect 634 (FIG. 6D) in sapphire structure 600 in operation 508, sapphire structure may be re-treated, or undergo at least some of the treating processes discussed in operation 502 again. That is, sapphire structure 600 may be re-lapped and/or re-polished again, such that terraced protrusions 610 formed during the annealing process in operation 504 may be substantially lapped and/or or polished. As shown in FIG. 6E, terraced protrusions 610 (shown in phantom) may be substantially removed from sapphire structure 600 as a result of re-treating top surface 602. That is, terrace protrusions 610 may be removed from top surface 602 as a result of the re-treating process in operation 510, where top surface 602 is substantially planar.

As shown in FIG. 6E, and discussed herein, the re-treating process in operation 510 may cause additional imperfections 644 in sapphire structure 600. More specifically, the re-treating (e.g., lapping, polishing) of sapphire structure 600 to remove terraced protrusions 610 including defect 634 may also cause new imperfections 644, such as crack 646, in sapphire structure 600.

In operation 512, sapphire structure 600 may be re-annealed in response to identifying defect 634 in sapphire structure 600 in operation 508, and/or re-treating top surface 602 in operation 510. As shown in FIGS. 6F and 6G, re-treated sapphire structure 600 may be re-annealed or annealed again as a result of identifying defect 634 in terraced protrusions 610 (FIG. 6D). However, the re-annealing process of operation 512 may be distinct from the annealing process in operation 504, in that that the re-annealing process of sapphire structure 600 may include adjusting annealing operational characteristics. More specifically, during the re-annealing of sapphire structure 600 in operation 512, at least one of the following annealing operational characteristics may be adjusted: the annealing temperature surrounding sapphire structure 600, the annealing time for sapphire structure 600, and/or the atmospheric pressure surrounding sapphire structure 600. By adjusting at least one of the annealing operational characteristics, the mobility of the surface atoms of sapphire structure 600 may be directly affected, which may ultimately cause affect the configuration or formation of distinct terraced protrusions 616 formed during the re-annealing process of operation 512.

For example, FIG. 6E may depict an re-annealing process performed on re-treated sapphire structure 600, where the annealing time is substantially lower in the re-annealing process of operation 512 than the annealing time used in operation 504 (e.g., FIG. 6B). As such, the surface atoms of top surface 602 of sapphire structure 600 may not have as much time to rearrange themselves during the re-annealing process of operation 512. As a result of the adjustment to the annealing time and/or reduced rearrangement time for the surface atoms, terraced protrusions 616 formed in the re-annealing process, as shown in FIG. 6F, may include an actual height ($H_{ACTL}$) and actual peak distance ($PD_{ACTL}$) substantially smaller than terraced protrusions 610 formed during the annealing process of operation 504 (FIG. 6D). Additionally, as a result of the adjustment of the annealing time during the re-annealing process in operation 512, terraced protrusions 616 may be subsequently inspected (operation 508) to determine if defect 634 (FIG. 6D) is still identifiable within sapphire structure 600 (operation 508). As shown in the embodiment depicted in FIG. 6E, terraced protrusions 616 of sapphire structure 600 may be substantially free from defect 634 (FIG. 6D). More specifically, the actual height ($H_{ACK}$) and peak distance ($PD_{ACTL}$) of terraced protrusions 616 do not exceed the respective predetermined acceptable height ($H_{ACPT}$) and peak distance ($P_{DACPT}$) of acceptable terraced protrusion 636 of sapphire structure 600. As such, sapphire structure 600 including terraced protrusions 616 formed on top surface 602 during the re-annealing process of operation 512 may be substantially free from defect 634 and may be acceptable for use within electronic device 10 (FIG. 1).

In operation 514, at least one decorative layer 650 may be deposited over at least a portion of re-treated, re-annealed sapphire structure 600. As shown in FIG. 6H, re-treated, re-annealed sapphire structure 600 include terraced protrusions 616 may include at least one deposited decorative layer 650. More specifically, in operation 514 decorative layer 650 may be deposited over at least a portion of terraced protrusions 616 formed in top surface 602 of sapphire structure 600. Decorative layer 650 may include paint, etching material, graphics, or any other conventional layer that may be deposited on at least a portion of top surface 602 including terraced protrusions 616 prior to sapphire structure 600 being implemented within electronic device 10 (FIG. 1). Decorative layer 650 may be deposited over at least a portion of top surface 602 of sapphire structure 600 using any conventional deposition technique including, but not limited to: chemical vapor deposition, spin coating, sputtering, or pulsed laser deposition.

As shown in FIG. 5, and discussed above, where defect 634 is not identified in top surface 602 of sapphire structure 600, at least one decorative layer 650 may be deposited on sapphire structure 600. That is, in an additional embodiment (not shown), sapphire structure 600 may not include defect 634 after performing the annealing process in operation 504. More specifically, and as similarly discussed with respect to annealed sapphire structure 400 in FIG. 4G, sapphire structure 600 may be substantially free from defect after performing the annealing process in operation 504. As such, while performing the inspection process in operation 506, and the identifying process in operation 508, it may be determined that sapphire structure 600 is substantially free from and/or may not include defect 634. As a result, sapphire structure 600, free from defect 634, may subsequently skip operation 510 and/or operation 512, and may proceed to the depositing of decorative layer 550 in operation 514.

Additionally as shown in FIG. 5, after defect 634 is identified in operation 508, operation 510 may be performed. However, operation 512 may or may not be performed before repeating the inspection process of operation 506. That is, and distinct from the discussion above with respect to FIGS. 6A-6H, top surface 602 of sapphire structure 600 including defect 634 may be re-treated in operation 510, and then may be subsequently re-inspected in operation 506, without re-annealed sapphire structure 600 in operation 512. The specific configuration or dimensional orientation of terraced protrusions 610 including defect 634 may determine if sapphire structure 600 may require re-annealing before being re-inspected. That is, the actual height ($H_{ACTL}$) and/or the actual peak distance ($PD_{ACTL}$) of terraced protrusions 610 may determine if the re-annealing of operation 512 may be performed. As discussed above with respect to FIGS. 6A-6H, where both the actual height ($H_{ACTL}$) and peak distance ($PD_{ACTL}$) of terraced protrusions 610 exceed the respective predetermined acceptable height ($H_{ACPT}$) and peak distance ($PD_{ACPT}$) of acceptable terraced protrusion 636, the re-annealing process of operation 512 may be performed on sapphire structure 600. Similarly, where only the actual peak distance ($PD_{ACTL}$) of terraced protrusions 610 exceeds the predetermined peak distance ($PD_{ACPT}$) of acceptable terraced protrusion 636, the re-annealing process of operation 512 may be performed on sapphire structure 600. However, where only the actual height ($H_{ACTL}$) of terraced protrusions 610 exceeds the predetermined height ($H_{ACPT}$) of acceptable terraced protrusion 636, the re-annealing process of operation 512 may not be performed on sapphire structure 600. As discussed above with respect to FIG. 4E, where only the actual height ($H_{ACTL}$) of terraced protrusions 610 exceeds the predetermined height ($H_{ACPT}$) of acceptable terraced protrusion 636, defect 634 may only be attributed to the height (H) of terraced protrusions 610. As such, the re-treating of sapphire structure 600 in operation 510 alone may correct defect 634. More specifically, by lapping and/or polishing off a top portion of terraced protrusions 610 of sapphire structure 600, terraced protrusions 610 may no longer include defect 634, and may be implemented within electronic device 10 (FIG. 1).

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

We claim:

1. A method of inspecting a sapphire structure, comprising:
    providing an annealed sapphire structure having a group of distinct terraced protrusions;
    measuring a profile of at least a portion of the annealed sapphire structure, the measuring comprising:
        detecting a set of height values of the group of distinct terraced protrusions; and
        detecting a set of distance values between peaks of the group of distinct terraced protrusions;
    determining an estimated crystallographic plane orientation for the annealed sapphire structure based on the set of height values and the set of distance values; and
    identifying a defect within at least a portion of the measured profile of the annealed sapphire structure using the estimated crystallographic plane orientation.

2. The method of claim 1, wherein the identifying of the defect further comprises at least one of:
    comparing the set of height values with a predetermined acceptable height; and
    comparing the set of distance values with a predetermined acceptable peak distance.

3. The method of claim 2, wherein the identifying of the defect within at least the portion of the measured profile of the annealed sapphire structure further comprises at least one of:
    determining the set of height values differs from the predetermined acceptable height; and
    determining the set of distance values differs from the predetermined acceptable peak distance.

4. The method of claim 2, wherein:
    the predetermined acceptable height includes a height of acceptable terraced protrusions for the annealed sapphire structure; and
    the acceptable terraced protrusions of the annealed sapphire structure are substantially free from the defect.

5. The method of claim 4, wherein:
    the predetermined acceptable peak distance includes a peak distance of the acceptable terraced protrusions for the annealed sapphire structure; and
    the acceptable terraced protrusions of the annealed sapphire structure are substantially free from the defect.

6. The method of claim 1, wherein the measuring of the profile further comprises:
    detecting the set of height and distance values using one of:
        a differential interference contrast (DIC) microscope;
        an interferometer; or
        a profilometer.

7. The method of claim 1, wherein the defect includes an optical defect formed in the top surface of the annealed sapphire structure.

8. A method of inspecting a sapphire substrate, comprising:
    providing an annealed sapphire substrate;
    inspecting a profile of a surface of the annealed sapphire substrate by detecting at least one of:
        a defect region defined by a first group of terraced protrusions indicating that a crystallographic plane orientation satisfies a first alignment condition with respect to the surface of the sapphire substrate; or
        a defect-free region defined by a second group of terraced protrusions indicating that the crystallographic plane orientation satisfies a second alignment condition with respect to the surface of the sapphire substrate; and
    in response to a detection of defect region, performing at least one surface treatment to the sapphire substrate.

9. The method of claim 8, wherein the performing the at least one surface treatment comprises:
    depositing at least one decorative layer over a portion of the sapphire substrate.

10. The method of claim 8, wherein the performing of the at least one surface treatment comprises:
    lapping a portion of the sapphire substrate; and
    polishing the lapped portion of the sapphire substrate.

11. The method of claim 8, wherein the performing of the at least one surface treatment comprises:
    re-annealing the sapphire substrate.

12. The method of claim 8, wherein the inspecting further comprises at least one of:
    comparing a set of height values of the first or second groups of distinct terraced protrusions with a predetermined acceptable height; and
    comparing a set of distance values of the first or second groups of distinct terraced protrusions with a predetermined acceptable peak distance.

13. The method or claim 12, wherein the inspecting further comprises at least one of:
    determining the set of height values of the first or second groups of distinct terraced protrusions differs from the predetermined acceptable height; and
    determining the set of distance values of the first or second groups of distinct terraced protrusions differs from the predetermined acceptable peak distance.

14. The method of claim 8, wherein the inspecting of the profile further comprises:
    detecting at least one of the defect region or the defect-free region using at least one of:
        a differential interference contrast (DIC) microscope;
        an interferometer; or
        a profilometer.

* * * * *